(12) United States Patent
Ben-Sasson

(10) Patent No.: US 6,833,436 B2
(45) Date of Patent: Dec. 21, 2004

(54) SHORT PEPTIDES WHICH SELECTIVELY MODULATE THE ACTIVITY OF SERINE/THREONINE KINASES

(75) Inventor: Shmuel A. Ben-Sasson, Jerusalem (IL)

(73) Assignees: Children's Medical Center Corporation, Boston, MA (US); Yissum Research Development Company of the Hebrew University of Jerusalem, Jerusalem (IL)

( * ) Notice: Subject to any disclaimer, the term of this patent is extended or adjusted under 35 U.S.C. 154(b) by 288 days.

(21) Appl. No.: 09/736,076

(22) Filed: Dec. 13, 2000

(65) Prior Publication Data

US 2002/0049301 A1 Apr. 25, 2002

Related U.S. Application Data

(63) Continuation-in-part of application No. 08/861,338, filed on May 21, 1997, now Pat. No. 6,174,993.

(51) Int. Cl.[7] ............................................. A61K 38/00
(52) U.S. Cl. ...................................................... 530/326
(58) Field of Search ......................................... 530/326

(56) References Cited

FOREIGN PATENT DOCUMENTS

| WO | WO 93/16703 A1 | 9/1993 |
|---|---|---|
| WO | WO 97/14038 A1 | 4/1997 |

OTHER PUBLICATIONS

Rudikoff et al. Single amino acid substitution altering antigen–binding specificity. Proc Natl Acad Sci U S A. Mar. 1982;79(6)1979–83.*
Kallunki et al, "JNK2 contains a specificity–determining region responsible for efficient c–Jun binding and phosphorylation", *Genes & Development* 8:2996–3007 (1994).
Hubbard et al, "Crystal structure of the tyrosine kinase domain of the human insulin receptor", *Nature* 372:746–753 (1994).
Kohn et al, Expression of a Constitutitively Active Akt Ser/Thr Kinase in 3T3–L1 Adipocytes Stimulates Glucose Uptake and Glucose Transporter 4 Translocation *J Biol Chem* 271(49):31372–31378 (1996).
Lange–Carter et al, "A Divergence in the MAP Kinase Regulatory Network efined by MEK Kinase and Raf", *Science* 260 315–318 (1993).
Lovrić et al, "Activation of Mil/Raf protein kinases in mitotic cells", *Oncogene* 12:1109–1116 (1996).
Mason IJ, "Th Ins and Outs of Fibroblast Growth Factors", *Cell* 78:547–552 (1994).
McMurray et al, "Cyclic peptide substrates of pp60c–src: synthesis and evaluation", *Int J Pept Protein Res* 42(3):209–215 (1993) (from *Chem Abastracts* 1993, Acc. No. 120:100177).

Mohammadi et al, "Structure of the FGF Receptor Tyrosine Kinase Domain Reveals a Novel Autoinhibitory Mechanism", *Cell* 86:577=587 (1996).
Nishizuka Y, "Protein kinase C and lipd signaling for substained cellular responses", *FASEB J* 9:484–496 (1995).
Okada et al, "Synthesis of Gln–Val–Val–Ala–Gly, a common sequence of thiol proteinase inhibitors, and its derivatives. Relationship between structure and effect on thiol proteinases", *Pept Chem* 653–656 (1998) (from *Chem Abstracts* , 1998, Acc. No. 109:69322).
Simmons et al, "Identification of an early–growth–response gene encoding a novel putative protein kinase", *Mol Cel Biol* 12(9):4164–4169 (1992).
Taylor et al, "cAMP–dependent protein kinase defines a family of enzymes", *Phil Trans R Soc Lond B* 340:315–324 (1993).
Alemá et al, "Differentation of PC12 phaeochromocytoma cells induced by v–src oncogene", *Nature* 316(6028):557–559 (1985).
Birchall et al, "Ro 32–0432, a Selective and Orally Active Inhibitor of Protein Kinase C Prevents T–Cell Activation", *J Parmacol Exp Ther* 268(2):922–929 (1994).
Bradshaw et al, "Therapeutic potential of protein kinase C inhibitors", *Agents Actions* 38(1–2):135–147 (1993).
Dudek et al, "Regulation of neuronal Survival by the Serine–Threonine Protein Kinase Akt", *Science* 275:661–665 (1997).
Franke et al, "P13K: Downstream AKTion Blocks Apoptosis", *Cell* 88:435–437 (1997).
Freedman et al, "Desensitization of G Protein–Coupled Receptors", *Recent Prog Horm Res* 51:319–353 (1996).
Ghiso et al, "Binding of Cystatin C to C4: The Importance of Sense–Antisense Peptides in their interaction", *Proc Nat Acad Sci USA* 87(4):1288–1294 (1990).
Glover et al, "Polo–Kinase: The Choreographer of the Mitotic Stage?", *J Cell Biol* 135:1681–1684 (1996).
Hanks et al, The Eukaryotic Protein Kinase Superfamily in *The Protein Kinase Facts Book*, vol. 1, Hardie et al, eds., Academic Press, Chapter 2 (1995).
Hemmings BA, "Akt Signaling: Linking Membrane Events to Life and Death Decisions", *Science* 275:628–631 (1997).

* cited by examiner

*Primary Examiner*—Christopher R. Tate
*Assistant Examiner*—Maury Audet
(74) *Attorney, Agent, or Firm*—Browdy and Neimark, PLLC

(57) ABSTRACT

Disclosed are peptides which are peptide derivatives of the HJ loop of a serine/threonine kinase. The peptides can modulate the activity of the serine/threonine kinase. Also disclosed are methods of modulating the activity of a serine/threonine kinase in a subject by administering one of the peptides of the present invention.

1 Claim, 9 Drawing Sheets

| 1 | 2 | 3 | 4 | 5 | 6 | 7 | 8 | 9 | 10 |
|---|---|---|---|---|---|---|---|---|---|
| Y/F | X | L/M | L/M/A/I | X | G/A | X | Hydrophobic | P | F/Y |

Figure 1

| 1 | 2 | 3 | 4 | 5 | 6 | 7 | 8 | 9 | 10 |
|---|---|---|---|---|---|---|---|---|---|
| Y | E | M | L/M/A | X | G | X | P | P | F |

| 11 | 12 | 13 | 14 | 15 | 16 | 17 | 18 | 19 | 20 |
|----|----|----|----|----|----|----|----|----|----|
| X | A/G | D/E/Q | D/E/Q/N | P/E | D/E/I | D/E/Q | I/L | Y/F | Q/E |

Figure 2

SERINE\THREONINE KINASES

|  | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|
| RAF | Y F W | E Q E* N D D* | L I M | M V L I | T A S | G A | E Q D E* D* | L I M | P | Y F W | S A T | H N D Q E E* | I L M V | N D* D Q E E* | N D* D Q E E* | R X | D N D* Q E E* | Q E E* N D D* | I L M V | I L M V |
| CAPK | Y F W | E Q E* D D* N | M V L I | A G | A V M L I | G A | Y F W | P | | P | F Y W | F Y W | A G | D N D* Q E E* | Q E N D* | P | I L M V | Q E E* N D D* | I L F M W | E Q E* N D D* |
| PKC | Y F W | E Q E* D D* N | M V L I | L M I V | A I C L M V | G A | Q H E E* | P A S | | P | F Y W | D E H Q N D* E* | G A | E D Q N D* E* | D Q E* N E D* | D E Q Q N D* E* | E D Q N D* E* | L I Q M N V | F Y M W | Q E H E* |
| βARK1.2 | F Y W | K Q O | L I M V | I L M V | R X | G A | H | S T | | P | F Y W | R Y X W | Q E D N E* D* | H | K O | T S | K O | D N D* Q E E* | K N O | H O | E Q N D D* E* |
| CaMK | Y F W | I L M V | L I M V | L I M C I | V L M | G A | Y F W | P | | P | F Y W | W Y F | D N D* Q E E* | E Q E* N D D* | D N D* Q E D E* | Q E E* D* N | H | R K X O | L I M V | Y F W | Q E E* D D* N |

Figure 3A

|       | 1 | 2  | 3 | 4 | 5  | 6 | 7 | 8 | 9 | 10 | 11 | 12 | 13 | 14 | 15 | 16 | 17 | 18 | 19 | 20 |
|-------|---|----|---|---|----|---|---|---|---|----|----|----|----|----|----|----|----|----|----|----|
| POLO  | Y | T  | L | L | V  | G | K | P | P | F  | E  | T  | S  | C  | L  | K  | E  | T  | Y  | L  |
|       | F | S  | M | I | L  | A | R |   |   | Y  | D  | S  | T  | V  | O  | D  | S  | F  | I  |    |
|       | W |    | I | M | I  |   | O |   |   | W  | Q  |    | S  | I  |    | N  |    | W  | V  |    |
|       |   |    | V | V | M  |   | X |   |   |    | N  |    |    | M  |    | Q  |    |    | M  |    |
|       |   |    |   |   |    |   |   |   |   |    | E* |    |    |    |    | E* |    |    |    |    |
|       |   |    |   |   |    |   |   |   |   |    | D* |    |    |    |    | D* |    |    |    |    |
| Akt/  | Y | E  | M | M | C  | G | R | L | P | F  | Y  | N  | Q  | D  | H  | E  | R  | L  | F  | E  |
| PKB   | F | E* | L | L | S  | A | X | M |   | W  | W  | Q  | N  | D* | K  | E* | X  | M  | Y  | E* |
|       | W | D  | I | I | T  |   |   | I |   |    | Y  |    |    | E  | O  | D  | K  | I  | W  | D  |
|       |   | D* | V | V |    |   |   | V |   |    | F  |    |    | E* |    | D* | O  | V  |    | D* |
| GRK1  | Y | E  | M | I | A  | A | R | G | P | F  | R  | A  | R  | G  | E  | K  | V  | E  | N  | K  |
|       | W | E* | I | M | G  | G | X | A |   | W  | X  | G  | X  | A  | E* | O  | M  | E* | Q  | O  |
|       | F | D  | L | L |    |   |   |   |   |    | Y  |    |    |    |    |    | D  | H  | I  | D  | H  |
|       |   | D* | V | V |    |   |   |   |   |    |    |    |    |    | D* |    |    | L  | D* |    |
| GRK4  | Y | E  | M | I | Q  | G | H | S | P | F  | K  | K  | Y  | K  | E  | K  | V  | K  | W  | E  |
|       | F | E* | I | L | N  | A | K | T |   | W  | O  | O  | F  | O  | E* | O  | M  | O  | F  | E* |
|       | W | D  | L | M |    |   | O |   |   |    | Y  | H  | H  | W  | D  | H  | I  | H  | Y  | D  |
|       |   | D* | V | V |    |   |   |   |   |    |    |    |    |    | D* |    | L  |    |    | D* |
| GRK5  | Y | E  | M | I | E  | G | Q | S | P | F  | R  | G  | R  | K  | E  | K  | V  | K  | R  | E  |
|       | F | E* | I | L | E* | A | N | T |   | W  | X  | A  | X  | O  | E* | O  | M  | O  | X  | E* |
|       | W | D  | L | M | D  |   |   |   |   |    | Y  |    |    | H  | D  | H  | I  | H  |    | D  |
|       |   | D* | V | V | D* |   |   |   |   |    |    |    |    |    | D* |    | L  |    |    | D* |
| GRK6  | Y | E  | M | I | A  | G | Q | S | P | F  | Q  | Q  | R  | K  | K  | K  | I  | K  | R  | E  |
|       | F | E* | I | L | G  | A | N | T |   | W  | N  | N  | X  | O  | O  | O  | M  | O  | X  | E* |
|       | W | D  | L | M |    |   |   |   |   |    | Y  |    |    |    | H  | H  | H  | V  | H  | D  |
|       |   | D* | V | V |    |   |   |   |   |    |    |    |    |    |    |    |    | L  |    | D* |
| GSK3  | A | E  | L | L | L  | G | Q | P | I | F  | P  | G  | D  | S  | G  | V  | D  | Q  | L  | V  |
|       | G | E* | I | I | I  | A | N |   | L | Y  |    | A  | D* | T  | A  | L  | D* | N  | I  | L  |
|       |   | D  | M | M | M  |   |   |   | M | W  |    |    | E  |    |    | I  | E  |    | M  | I  |
|       |   | D* | V | V | V  |   |   |   | V |    |    |    | E* |    |    | M  | E* |    | V  | M  |

D* = a substituted or unsubstituted aliphatic, benzylic or aromatic ester of aspartic acid  
E* = a substituted or unsubstituted aliphatic, benzylic or aromatic ester of glutamic acid  
X  = N-nitroargine, β-cycloarginine, γ-hydroxyarginine, amidinocitroline or 2-amino-4-guanidinobutanoic acid  
O  = Ornithine

Figure 3B

RAF

| | | | | | | | | | | |
|---|---|---|---|---|---|---|---|---|---|---|
| HJ38 | Ac- | | V | M | T | G | Q' | L | P | F | -NH₂ |
| J41 | Ac- | | V | M | T | G | E! | L | P | F | -NH₂ |

POLO

| | | | | | | | | | | | | |
|---|---|---|---|---|---|---|---|---|---|---|---|---|
| J42 | Ac- | | M | L | L | G | R | P | P | F | E! | -NH₂ |
| J43 | Ac- | | M | L | L | G | K | P | P | F | NH₂ | |
| J43.1 | Ac- | | M | L | L | G | K | P | P | F | E! | -NH₂ |
| J45 | | Ac- | L | | | G | R | P | P | F | E! | T | S | -NH₂ |
| J46 | Ac- | | M | L | L | G | R | P | P | F | E! | T | S | -NH₂ |

AkT/PKB

| | | | | | | | | | | | |
|---|---|---|---|---|---|---|---|---|---|---|---|
| J47 | | | Ac- | | G | R | L | P | F | F | N | -NH₂ |
| J48 | Ac- | E! | M | M | S | G | R | L | P | F | F | N | -NH₂ |

GSK3

| | | | | | | | | | | |
|---|---|---|---|---|---|---|---|---|---|---|
| J29 | Ac- | L | L | L | G | Q | P | I | F | P | G | -NH₂ |

E! - Benzyl Ester of Glutamic Acid

Figure 4

Activin/TGFbR
ACTRII

| | Peptide | N_terminal | | C_terminal |
|---|---|---|---|---|
| | K095H101 | Myristyl - G | G P V D E Y M L P F | NH2 |

ALK1

| | Peptide | N_terminal | | C_terminal |
|---|---|---|---|---|
| | K048H101 | Myristyl - G | G I V E D Y R P P F | NH2 |
| | K048H901 | Stearyl - G | G I V E D Y R P P F | NH2 |

ALK3

| | Peptide | N_terminal | | C_terminal |
|---|---|---|---|---|
| | K098H101 | Myristyl - G | G I V E E Y Q L P Y | NH2 |
| | K098H901 | Stearyl - G | G I V E E Y Q L P Y | NH2 |

ALK4

| | Peptide | N_terminal | | C_terminal |
|---|---|---|---|---|
| | K099H101 | Myristyl - G | G Q V H E E Y Q L P Y | NH2 |

TGFbRII

| | Peptide | N_terminal | | C_terminal |
|---|---|---|---|---|
| | K093H101 | Myristyl - G | G E V K D Y E P P F | NH2 |

Akt/PKB
Akt1/Raca

| | Peptide | N_terminal | | C_terminal |
|---|---|---|---|---|
| | K014H101 | Myristyl - G | M M S G R L P | NH2 |
| | K014H010 | (Free NH2) | M C G R L P | NH2 |
| | K014H111 | Myristyl - G | M M C G R L P | NH2 |

CAPK
cAPKa

| | Peptide | N_terminal | | C_terminal |
|---|---|---|---|---|
| | K004H001 | Acetyl | M A A G Y P | NH2 |
| | K004H002 | Acetyl | M A A G Y P P F F | NH2 |

CDK

Figure 6A

CDK2

| | Peptide | N_terminal | | C_terminal |
|---|---|---|---|---|
| | K049H101 | Myristyl-G | M V T R R A L F | NH2 |

CDK4

| | Peptide | N_terminal | | C_terminal |
|---|---|---|---|---|
| | K050H101 | Myristyl-G | M F R R K P L F | NH2 |

CHK
Chk1

| | Peptide | N_terminal | | C_terminal |
|---|---|---|---|---|
| | K088H001 | Acetyl | M L A G E! L P W D! | NH2 |
| | K088H101 | Myristyl-G | M L A G E L P | NH2 |
| | K088H103 | Myristyl-G | M L A G E L | NH2 |
| | K088H104 | Myristyl-G | M L A G E L P W D | NH2 |

DAPK
DAPK

| | Peptide | N_terminal | | C_terminal |
|---|---|---|---|---|
| | K092H001 | Acetyl | I L L S G A S P F L G | NH2 |

GRK
bARK1

| | Peptide | N_terminal | | C_terminal |
|---|---|---|---|---|
| | K024H101 | Myristyl-G | L L R G H S | NH2 |

GSK3
GSK3b

| | Peptide | N_terminal | | C_terminal |
|---|---|---|---|---|
| | K018H101 | Myristyl-G | L L L G Q P I | NH2 |

IAK
Iak1

| | Peptide | N_terminal | | C_terminal |
|---|---|---|---|---|
| | K087H001 | Acetyl | F L V G M P P F | NH2 |
| | K087H101 | Myristyl-G | F L V G M P P | NH2 |
| | K087H102 | Myristyl-G | F L V G M P | NH2 |

Figure 6B

| | | Peptide N_terminal | | C_terminal |
|---|---|---|---|---|
| IKK | | | | |
| IKK-1 | K087H103 | Myristyl -G | F L V G M P P F E | NH2 |
| | | Peptide N_terminal | | C_terminal |
| | K090H101 | Myristyl - G | I A G Y R P F L | NH2 |
| IKK-2 | | | | |
| | | Peptide N_terminal | | C_terminal |
| | K091H001 | Acetyl | I T G F R P F L | NH2 |
| | K091H101 | Myristyl -G | I T G F R P F L | NH2 |
| ILK | | | | |
| ILK | | Peptide N_terminal | | C_terminal |
| | K107H001 | Acetyl | L V T R E! V | NH2 |
| | K107H101 | Myristyl -G | L V T R E V P F | NH2 |
| | K107H102 | Myristyl - G | L V T R E V | NH2 |
| | K107H901 | Stearyl - G | L V T R E V P F | NH2 |
| MARK/p78 | | | | |
| MARK1 | | Peptide N_terminal | | C_terminal |
| | K045H101 | Myristyl -G | L V S G S | NH2 |
| | K045H102 | Myristyl -G | L V S G S L P | NH2 |
| PKC | | | | |
| PKCb | | Peptide N_terminal | | C_terminal |
| | K008H001 | Acetyl | M L A G Q A P F | NH2 |
| | K008H101 | Myristyl -G | M L A G Q A P | NH2 |
| | K008H102 | Myristyl -G | M L A G Q A | NH2 |
| | K008H103 | Myristyl -G | M L A G Q A P F E | NH2 |

Figure 6C

POLO
Plk

| | Peptide | N_terminal | | C_terminal |
|---|---|---|---|---|
| | K035H001 | Acetyl | L L V G K P P F | NH2 |
| | K035H101 | Myristyl -G | L L V G K P P | NH2 |

SNK

| | Peptide | N_terminal | | C_terminal |
|---|---|---|---|---|
| | K038H101 | Myristyl -G | M L L G R P P F E! | NH2 |
| | K038H102 | Myristyl -G | M L L G R P P | NH2 |

RAF
Braf

| | Peptide | N_terminal | | C_terminal |
|---|---|---|---|---|
| | K003H103 | Myristyl -G | L M T G Q L | NH2 |
| | K003H104 | Myristyl -G | L M T G Q L P Y S | NH2 | c-Raf

| | Peptide | N_terminal | | C_terminal |
|---|---|---|---|---|
| | K001H102 | Myristyl -G | L M T G E L | NH2 |
| | K001H103 | Myristyl -G | L M T G E L P Y S | NH2 |

SEQUENCE LISTING

<160> NUMBER OF SEQ ID NOS: 68

<210> SEQ ID NO 1
<211> LENGTH: 20
<212> TYPE: PRT
<213> ORGANISM: Unknown
<220> FEATURE:
<223> OTHER INFORMATION: RAF

<400> SEQUENCE: 1

Tyr Glu Leu Met Thr Gly Glu Leu Pro Tyr Ser His Ile Asn Asn Arg
1               5                   10                  15

Asp Gln Ile Ile
            20

<210> SEQ ID NO 2
<211> LENGTH: 20
<212> TYPE: PRT
<213> ORGANISM: Unknown
<220> FEATURE:
<223> OTHER INFORMATION: CAPK

<400> SEQUENCE: 2

Tyr Glu Met Ala Ala Gly Tyr Pro Pro Phe Phe Ala Asp Gln Pro Ile
1               5                   10                  15

Gln Ile Tyr Glu
            20

<210> SEQ ID NO 3
<211> LENGTH: 20
<212> TYPE: PRT
<213> ORGANISM: Unknown
<220> FEATURE:
<223> OTHER INFORMATION: PKC

<400> SEQUENCE: 3

Tyr Glu Met Leu Ala Gly Gln Pro Pro Phe Asp Gly Glu Asp Glu Asp
1               5                   10                  15

Glu Leu Phe Gln
            20

<210> SEQ ID NO 4
<211> LENGTH: 20
<212> TYPE: PRT
<213> ORGANISM: Unknown
<220> FEATURE:
<223> OTHER INFORMATION: bARK1.2

<400> SEQUENCE: 4

Phe Lys Leu Ile Arg Gly His Ser Pro Phe Arg Gln His Lys Thr Lys
1               5                   10                  15

Asp Lys His Glu
            20

<210> SEQ ID NO 5
<211> LENGTH: 20
<212> TYPE: PRT
<213> ORGANISM: Unknown
<220> FEATURE:
<223> OTHER INFORMATION: CaMK

<400> SEQUENCE: 5

Tyr Ile Leu Leu Val Gly Tyr Pro Pro Phe Trp Asp Glu Asp Gln His

```
                1               5                  10                 15
Arg Leu Tyr Gln
            20

<210> SEQ ID NO 6
<211> LENGTH: 20
<212> TYPE: PRT
<213> ORGANISM: Unknown
<220> FEATURE:
<223> OTHER INFORMATION: POLO

<400> SEQUENCE: 6

Tyr Thr Leu Leu Val Gly Lys Pro Pro Phe Glu Thr Ser Cys Leu Lys
  1               5                  10                 15

Glu Thr Tyr Leu
            20

<210> SEQ ID NO 7
<211> LENGTH: 20
<212> TYPE: PRT
<213> ORGANISM: Unknown
<220> FEATURE:
<223> OTHER INFORMATION: Akt/PKB

<400> SEQUENCE: 7

Tyr Glu Met Met Cys Gly Arg Leu Pro Phe Tyr Asn Gln Asp His Glu
  1               5                  10                 15

Arg Leu Phe Glu
            20

<210> SEQ ID NO 8
<211> LENGTH: 20
<212> TYPE: PRT
<213> ORGANISM: Unknown
<220> FEATURE:
<223> OTHER INFORMATION: GRK1

<400> SEQUENCE: 8

Tyr Glu Met Ile Ala Ala Arg Gly Pro Phe Arg Ala Arg Gly Glu Lys
  1               5                  10                 15

Val Glu Asn Lys
            20

<210> SEQ ID NO 9
<211> LENGTH: 20
<212> TYPE: PRT
<213> ORGANISM: Unknown
<220> FEATURE:
<223> OTHER INFORMATION: GRK4

<400> SEQUENCE: 9

Tyr Glu Met Ile Gln Gly His Ser Pro Phe Lys Lys Tyr Lys Glu Lys
  1               5                  10                 15

Val Lys Trp Glu
            20

<210> SEQ ID NO 10
<211> LENGTH: 20
<212> TYPE: PRT
<213> ORGANISM: Unknown
<220> FEATURE:
<223> OTHER INFORMATION: GRK5

<400> SEQUENCE: 10
```

-continued

Tyr Glu Met Ile Glu Gly Gln Ser Pro Phe Arg Gly Arg Lys Glu Lys
1               5                   10                  15

Val Lys Arg Glu
            20

<210> SEQ ID NO 11
<211> LENGTH: 20
<212> TYPE: PRT
<213> ORGANISM: Unknown
<220> FEATURE:
<223> OTHER INFORMATION: GRK6

<400> SEQUENCE: 11

Tyr Glu Met Ile Ala Gly Gln Ser Pro Phe Gln Gln Arg Lys Lys Lys
1               5                   10                  15

Ile Lys Arg Glu
            20

<210> SEQ ID NO 12
<211> LENGTH: 20
<212> TYPE: PRT
<213> ORGANISM: Unknown
<220> FEATURE:
<223> OTHER INFORMATION: GSK3

<400> SEQUENCE: 12

Ala Glu Leu Leu Leu Gly Gln Pro Ile Phe Pro Gly Asp Ser Gly Val
1               5                   10                  15

Asp Gln Leu Val
            20

<210> SEQ ID NO 13
<211> LENGTH: 8
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(8)
<223> OTHER INFORMATION: HJ38

<400> SEQUENCE: 13

Val Met Thr Gly Gln Leu Pro Phe
1               5

<210> SEQ ID NO 14
<211> LENGTH: 8
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: position 5 is benzylester
<221> NAME/KEY: AMIDATION
<222> LOCATION: (0)...(8)
<223> OTHER INFORMATION: HJ41

<400> SEQUENCE: 14

Val Met Thr Gly Glu Leu Pro Phe
1               5

<210> SEQ ID NO 15
<211> LENGTH: 9
<212> TYPE: PRT
<213> ORGANISM: Artificial Sequence
<220> FEATURE:

```
<221> NAME/KEY: ACETYLATION
<222> LOCATION: (1)...(0)
<223> OTHER INFORMATION: position 9 is benzylester
<221> NAME/KEY: AMIDATION
<222> LOCATION: (0)...(9)
<223> OTHER INFORMATION: J42

<400> SEQUENCE: 15

Met Leu Leu Gly Arg Pro Pro Phe Glu
 1               5

<210> SEQ ID NO 16
<211> LENGTH: 8
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(8)
<223> OTHER INFORMATION: J43

<400> SEQUENCE: 16

Met Leu Leu Gly Lys Pro Pro Phe
 1               5

<210> SEQ ID NO 17
<211> LENGTH: 9
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: position 9 is benzylester
<221> NAME/KEY: AMIDATION
<222> LOCATION: (0)...(9)
<223> OTHER INFORMATION: J43.1

<400> SEQUENCE: 17

Met Leu Leu Gly Lys Pro Pro Phe Glu
 1               5

<210> SEQ ID NO 18
<211> LENGTH: 9
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: position 7 is benzylester
<221> NAME/KEY: AMIDATION
<222> LOCATION: (0)...(9)
<223> OTHER INFORMATION: J45

<400> SEQUENCE: 18

Leu Gly Arg Pro Pro Phe Glu Thr Ser
 1               5

<210> SEQ ID NO 19
<211> LENGTH: 11
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: position 9 is benzylester
<221> NAME/KEY: AMIDATION
<222> LOCATION: (0)...(11)
<223> OTHER INFORMATION: J46

<400> SEQUENCE: 19
```

```
Met Leu Leu Gly Arg Pro Pro Phe Glu Thr Ser
1               5                   10

<210> SEQ ID NO 20
<211> LENGTH: 7
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(7)
<223> OTHER INFORMATION: J47

<400> SEQUENCE: 20

Gly Arg Leu Pro Phe Phe Asn
1               5

<210> SEQ ID NO 21
<211> LENGTH: 11
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: position 1 is benzylester
<221> NAME/KEY: AMIDATION
<222> LOCATION: (0)...(11)
<223> OTHER INFORMATION: J48

<400> SEQUENCE: 21

Glu Met Met Ser Gly Arg Leu Pro Phe Phe Asn
1               5                   10

<210> SEQ ID NO 22
<211> LENGTH: 10
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(10)
<223> OTHER INFORMATION: J29

<400> SEQUENCE: 22

Leu Leu Leu Gly Gln Pro Ile Phe Pro Gly
1               5                   10

<210> SEQ ID NO 23
<211> LENGTH: 11
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(11)
<223> OTHER INFORMATION: ACTRIIA

<400> SEQUENCE: 23

Gly Gly Pro Val Asp Glu Tyr Met Leu Pro Phe
1               5                   10

<210> SEQ ID NO 24
<211> LENGTH: 11
<212> TYPE: PRT
<213> ORGANISM: Artificial Sequence
<220> FEATURE:
```

```
<221> NAME/KEY: MYRISTATE
<222> LOCATION: (1)...(0)
<221> NAME/KEY: AMIDATION
<222> LOCATION: (0)...(11)
<223> OTHER INFORMATION: ALK1

<400> SEQUENCE: 24

Gly Gly Ile Val Glu Asp Tyr Arg Pro Pro Phe
1               5                   10

<210> SEQ ID NO 25
<211> LENGTH: 11
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(11)
<223> OTHER INFORMATION: ALK3

<400> SEQUENCE: 25

Gly Gly Ile Val Glu Glu Tyr Gln Leu Pro Tyr
1               5                   10

<210> SEQ ID NO 26
<211> LENGTH: 12
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(12)
<223> OTHER INFORMATION: ALK4

<400> SEQUENCE: 26

Gly Gly Gln Val His Glu Glu Tyr Gln Leu Pro Tyr
1               5                   10

<210> SEQ ID NO 27
<211> LENGTH: 11
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(11)
<223> OTHER INFORMATION: TGFbRII

<400> SEQUENCE: 27

Gly Gly Glu Val Lys Asp Tyr Glu Pro Pro Phe
1               5                   10

<210> SEQ ID NO 28
<211> LENGTH: 8
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: ATK1/Racca

<400> SEQUENCE: 28

Gly Met Met Ser Gly Arg Leu Pro
1               5
```

```
<210> SEQ ID NO 29
<211> LENGTH: 6
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(6)
<223> OTHER INFORMATION: cAPKa

<400> SEQUENCE: 29

Met Ala Ala Gly Tyr Pro
1               5

<210> SEQ ID NO 30
<211> LENGTH: 9
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(9)
<223> OTHER INFORMATION: cAPKa

<400> SEQUENCE: 30

Met Ala Ala Gly Tyr Pro Pro Phe Phe
1               5

<210> SEQ ID NO 31
<211> LENGTH: 9
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(9)
<223> OTHER INFORMATION: CDK2

<400> SEQUENCE: 31

Gly Met Val Thr Arg Arg Ala Leu Phe
1               5

<210> SEQ ID NO 32
<211> LENGTH: 9
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(9)
<223> OTHER INFORMATION: CDK4

<400> SEQUENCE: 32

Gly Met Phe Arg Arg Lys Pro Leu Phe
1               5

<210> SEQ ID NO 33
<211> LENGTH: 9
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(9)
<223> OTHER INFORMATION: Chk1
```

```
<400> SEQUENCE: 33

Met Leu Ala Gly Glu Leu Pro Trp Asp
1               5

<210> SEQ ID NO 34
<211> LENGTH: 8
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: Chk1

<400> SEQUENCE: 34

Gly Met Leu Ala Gly Glu Leu Pro
1               5

<210> SEQ ID NO 35
<211> LENGTH: 7
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(7)
<223> OTHER INFORMATION: Chk1

<400> SEQUENCE: 35

Gly Met Leu Ala Gly Glu Leu
1               5

<210> SEQ ID NO 36
<211> LENGTH: 10
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(10)
<223> OTHER INFORMATION: Chk1

<400> SEQUENCE: 36

Gly Met Leu Ala Gly Glu Leu Pro Trp Asp
1               5                   10

<210> SEQ ID NO 37
<211> LENGTH: 11
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(11)
<223> OTHER INFORMATION: DAPK

<400> SEQUENCE: 37

Ile Leu Leu Ser Gly Ala Ser Pro Phe Leu Gly
1               5                   10

<210> SEQ ID NO 38
<211> LENGTH: 8
<212> TYPE: PRT
<213> ORGANISM: Artificial Sequence
```

```
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: GSK3b

<400> SEQUENCE: 38

Gly Leu Leu Leu Gly Gln Pro Ile
 1               5

<210> SEQ ID NO 39
<211> LENGTH: 8
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(8)
<223> OTHER INFORMATION: lak1

<400> SEQUENCE: 39

Phe Leu Val Gly Met Pro Pro Phe
 1               5

<210> SEQ ID NO 40
<211> LENGTH: 8
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: lak1

<400> SEQUENCE: 40

Gly Phe Leu Val Gly Met Pro Pro
 1               5

<210> SEQ ID NO 41
<211> LENGTH: 7
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(7)
<223> OTHER INFORMATION: lak1

<400> SEQUENCE: 41

Gly Phe Leu Val Gly Met Pro
 1               5

<210> SEQ ID NO 42
<211> LENGTH: 10
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(10)
<223> OTHER INFORMATION: lak1

<400> SEQUENCE: 42

Gly Phe Leu Val Gly Met Pro Pro Phe Glu
 1               5                  10
```

<210> SEQ ID NO 43
<211> LENGTH: 9
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(9)
<223> OTHER INFORMATION: IKK-1

<400> SEQUENCE: 43

Gly Ile Ala Gly Tyr Arg Pro Phe Leu
1               5

<210> SEQ ID NO 44
<211> LENGTH: 8
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(8)
<223> OTHER INFORMATION: IKK-2

<400> SEQUENCE: 44

Ile Thr Gly Phe Arg Pro Phe Leu
1               5

<210> SEQ ID NO 45
<211> LENGTH: 9
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(9)
<223> OTHER INFORMATION: IKK-2

<400> SEQUENCE: 45

Gly Ile Thr Gly Phe Arg Pro Phe Leu
1               5

<210> SEQ ID NO 46
<211> LENGTH: 6
<212> TYPE: PRT
<213> ORGANISM: Artificial Sequence
<220> FEATURE:
<221> NAME/KEY: ACETYLATION
<222> LOCATION: (1)...(0)
<223> OTHER INFORMATION: position 5 is benzylester
<221> NAME/KEY: AMIDATION
<222> LOCATION: (0)...(6)
<223> OTHER INFORMATION: ILK

<400> SEQUENCE: 46

Leu Val Thr Arg Glu Val
1               5

<210> SEQ ID NO 47
<211> LENGTH: 9
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION

```
<222> LOCATION: (0)...(9)
<223> OTHER INFORMATION: ILK

<400> SEQUENCE: 47

Gly Leu Val Thr Arg Glu Val Pro Phe
 1               5

<210> SEQ ID NO 48
<211> LENGTH: 7
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(7)
<223> OTHER INFORMATION: ILK

<400> SEQUENCE: 48

Gly Leu Val Thr Arg Glu Val
 1               5

<210> SEQ ID NO 49
<211> LENGTH: 6
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(6)
<223> OTHER INFORMATION: MARK1

<400> SEQUENCE: 49

Gly Leu Val Ser Gly Ser
 1               5

<210> SEQ ID NO 50
<211> LENGTH: 8
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: MARK1

<400> SEQUENCE: 50

Gly Leu Val Ser Gly Ser Leu Pro
 1               5

<210> SEQ ID NO 51
<211> LENGTH: 8
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(8)
<223> OTHER INFORMATION: PKCb

<400> SEQUENCE: 51

Met Leu Ala Gly Gln Ala Pro Phe
 1               5

<210> SEQ ID NO 52
<211> LENGTH: 8
```

```
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: PKCb

<400> SEQUENCE: 52

Gly Met Leu Ala Gly Gln Ala Pro
 1               5

<210> SEQ ID NO 53
<211> LENGTH: 7
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(7)
<223> OTHER INFORMATION: PKCb

<400> SEQUENCE: 53

Gly Met Leu Ala Gly Gln Ala
 1               5

<210> SEQ ID NO 54
<211> LENGTH: 10
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(10)
<223> OTHER INFORMATION: PKCb

<400> SEQUENCE: 54

Gly Met Leu Ala Gly Gln Ala Pro Phe Glu
 1               5                  10

<210> SEQ ID NO 55
<211> LENGTH: 8
<212> TYPE: PRT
<213> ORGANISM: Artificial Sequence
<220> FEATURE:
<221> NAME/KEY: ACETYLATION
<222> LOCATION: (1)...(0)
<221> NAME/KEY: AMIDATION
<222> LOCATION: (0)...(8)
<223> OTHER INFORMATION: Plk

<400> SEQUENCE: 55

Leu Leu Val Gly Lys Pro Pro Phe
 1               5

<210> SEQ ID NO 56
<211> LENGTH: 8
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: Plk

<400> SEQUENCE: 56
```

```
Gly Leu Leu Val Gly Lys Pro Pro
 1               5
```

```
<210> SEQ ID NO 57
<211> LENGTH: 10
<212> TYPE: PRT
<213> ORGANISM: Artificial Sequence
<220> FEATURE:
<221> NAME/KEY: MYRISTATE
<222> LOCATION: (1)...(0)
<223> OTHER INFORMATION: position 10 is benzylester
<221> NAME/KEY: AMIDATION
<222> LOCATION: (0)...(10)
<223> OTHER INFORMATION: SNK

<400> SEQUENCE: 57

Gly Met Leu Leu Gly Arg Pro Pro Phe Glu
 1               5                  10
```

```
<210> SEQ ID NO 58
<211> LENGTH: 8
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(8)
<223> OTHER INFORMATION: SNK

<400> SEQUENCE: 58

Gly Met Leu Leu Gly Arg Pro Pro
 1               5
```

```
<210> SEQ ID NO 59
<211> LENGTH: 7
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(7)
<223> OTHER INFORMATION: Braf

<400> SEQUENCE: 59

Gly Leu Met Thr Gly Gln Leu
 1               5
```

```
<210> SEQ ID NO 60
<211> LENGTH: 10
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(10)
<223> OTHER INFORMATION: Braf

<400> SEQUENCE: 60

Gly Leu Met Thr Gly Gln Leu Pro Tyr Ser
 1               5                  10
```

```
<210> SEQ ID NO 61
<211> LENGTH: 7
<212> TYPE: PRT
<213> ORGANISM: Artificial Sequence
<220> FEATURE:
<221> NAME/KEY: MYRISTATE
```

```
<222> LOCATION: (1)...(0)
<221> NAME/KEY: AMIDATION
<222> LOCATION: (0)...(7)
<223> OTHER INFORMATION: cRaf

<400> SEQUENCE: 61

Gly Leu Met Thr Gly Glu Leu
 1               5

<210> SEQ ID NO 62
<211> LENGTH: 10
<212> TYPE: PRT
<213> ORGANISM: Artificial Sequence
<220> FEATURE:
<221> NAME/KEY: MYRISTATE
<222> LOCATION: (1)...(0)
<221> NAME/KEY: AMIDATION
<222> LOCATION: (0)...(10)
<223> OTHER INFORMATION: cRaf

<400> SEQUENCE: 62

Gly Leu Met Thr Gly Glu Leu Pro Tyr Ser
 1               5                  10

<210> SEQ ID NO 63
<211> LENGTH: 6
<212> TYPE: PRT
<213> ORGANISM: Artificial Sequence
<220> FEATURE:
<223> OTHER INFORMATION: Akt1/Raca
<221> NAME/KEY: AMIDATION
<222> LOCATION: (0)...(6)

<400> SEQUENCE: 63

Met Cys Gly Arg Leu Pro
 1               5

<210> SEQ ID NO 64
<211> LENGTH: 8
<212> TYPE: PRT
<213> ORGANISM: Artificial Sequence
<220> FEATURE:
<223> OTHER INFORMATION: Akt1/Raca
<221> NAME/KEY: MYRISTATE
<222> LOCATION: (1)...(0)
<221> NAME/KEY: AMIDATION
<222> LOCATION: (0)...(8)

<400> SEQUENCE: 64

Gly Met Met Cys Gly Arg Leu Pro
 1               5

<210> SEQ ID NO 65
<211> LENGTH: 7
<212> TYPE: PRT
<213> ORGANISM: Artificial Sequence
<220> FEATURE:
<223> OTHER INFORMATION: bARK1
<221> NAME/KEY: MYRISTATE
<222> LOCATION: (1)...(0)
<221> NAME/KEY: AMIDATION
<222> LOCATION: (0)...(7)

<400> SEQUENCE: 65

Gly Leu Leu Arg Gly His Ser
 1               5

<210> SEQ ID NO 66
<211> LENGTH: 11
```

```
<212> TYPE: PRT
<213> ORGANISM: Artificial Sequence
<220> FEATURE:
<221> NAME/KEY: AMIDATION
<222> LOCATION: (0)...(11)
<223> OTHER INFORMATION: ALK1
      Stearate at position 1

<400> SEQUENCE: 66

Gly Gly Ile Val Glu Asp Tyr Arg Pro Pro Phe
 1               5                  10

<210> SEQ ID NO 67
<211> LENGTH: 11
<212> TYPE: PRT
<213> ORGANISM: Artificial Sequence
<220> FEATURE:
<223> OTHER INFORMATION: ALK3
      Stearate at position 1
<221> NAME/KEY: AMIDATION
<222> LOCATION: (0)...(11)

<400> SEQUENCE: 67

Gly Gly Ile Val Glu Glu Tyr Gln Leu Pro Tyr
 1               5                  10

<210> SEQ ID NO 68
<211> LENGTH: 9
<212> TYPE: PRT
<213> ORGANISM: Artificial Sequence
<220> FEATURE:
<223> OTHER INFORMATION: ILK
      Stearate at position 1
<221> NAME/KEY: AMIDATION
<222> LOCATION: (0)...(9)

<400> SEQUENCE: 68

Gly Leu Val Thr Arg Glu Val Pro Phe
 1               5
```

SHORT PEPTIDES WHICH SELECTIVELY MODULATE THE ACTIVITY OF SERINE/THREONINE KINASES

RELATED APPLICATIONS

This application is a continuation-in-part of U.S. Ser. No. 08/861,338, filed May 21, 1997, now U.S. Pat. No. 6,174,993, the entire teachings of which are incorporated herein by reference.

BACKGROUND OF THE INVENTION

Serine/threonine kinases are a member of the eukaryotic protein kinase superfamily. Enzymes of this class specifically phosphorylate serine or threonine residues of intracellular proteins and are important in mediating signal transduction in multicellular organisms. Many serine/threonine kinases occur as intracellular proteins which take part in signal transduction within the cell, including signal transduction to the nucleus and the activation of other proteins. Other serine/threonine kinases, such as G protein-coupled receptor kinases, are found in cell membranes and participate in transmembrane signalling.

As such, phosphorylation of serine or threonine by serine/threonine kinases is an important mechanism for regulating intracellular events in response to environmental changes. A wide variety of cellular events are regulated by serine/theronine kinases. A few examples include the ability of cells to enter and/or complete mitosis, cellular proliferation, cellular differentiation, the control of fat metabolism, immune responses, inflammatory responses and the control of glycogen metabolism.

Thus, agents which can modulate (increase or decrease) the activity of serine/threonine kinases have great potential for the treatment of a wide variety of diseases and conditions such as cancer, obesity, autoimmune disorders, inflammation and Type II diabetes.

SUMMARY OF THE INVENTION

It has now been found that short peptides which are derivatives of the HJ loop of a serine/threonine kinase can significantly affect the activities of cells expressing the serine/threonine kinase ("HJ loop" is defined hereinbelow). For example, the peptide derivatives of the HJ loop of Raf and Polo inhibit the proliferation of bovine aortic cells and the transformed mouse cell lines MS1 and/or SVR cells in vitro at concentrations as low as 10 μM (Example 2). Based on the aforementioned discoveries, novel peptides are disclosed herein which are peptide derivatives of the HJ loop of serine/threonine kinases. Also disclosed are methods of identifying a peptide derivative of an HJ loop of a serine/threonine kinase which modulates the activity of said serine/threonine kinase. Methods of modulating the activity of a serine/threonine kinase in a subject are also disclosed.

One embodiment of the present invention is a novel peptide which is a peptide derivative of the HJ loop of a serine/threonine kinase. The peptide comprises between about five and about twenty amino acid residues or amino acid residue analogs and modulates the activity of the serine/threonine kinase. The N-terminus and/or C-terminus of the peptide can be substituted or unsubstituted. The peptide can be linear or cyclic.

Another embodiment of the present invention is a method of modulating the activity of a serine/threonine kinase in a subject. The method comprises administering a therapeutically effective amount of a peptide which is a derivative of an HJ loop of said serine/threonine kinase, as described above.

Yet another embodiment of the present invention is a method of identifying a peptide which modulates the activity of a serine/threonine kinase. The method comprises providing a "test peptide" which has from about five to about twenty amino acids or amino acid analogs and which is a peptide derivative of the HJ loop of said serine/threonine kinase. The test peptide is incubated with cells having a cellular activity or function under the control of said serine/threonine kinase under conditions suitable for assessing the activity of the serine/threonine kinase. The activity of the serine/threonine kinase is assessed and compared with cells of the same cell type grown under the same conditions in the absence of the test peptide. A greater or lesser activity compared with cells grown in the absence of the test peptide indicates that the test peptide modulates activity of the serine/threonine kinase.

The peptides of the present invention can be used in the treatment of a wide variety of diseases caused by overactivity and underactivity of a STK. Examples include, but are not limited to, cancer, diabetes, obesity, diseases of the central nervous system, inflammatory disorders, autoimmune diseases and cardiovascular diseases. The peptides of the present invention also have in vitro utilities, for example, in the generation of antibodies which specifically bind the serine/threonine kinase from which the peptide was derived. These antibodies can be used to identify cells expressing the serine/threonine kinase and to study the intracellular distribution of the serine/threonine kinase. In addition, the peptides of the present invention can be used to identity and quantitate ligands which bind the NJ loop of the serine/threonine kinase from which the peptide was derived.

BRIEF DESCRIPTION OF THE FIGURES

FIG. 1 is a sequence illustrating the consensus sequence for amino acid one through amino acid ten of the HJ loop found among the family of serine/threonine kinases.

FIG. 2 is a sequence illustrating the consensus sequence for amino acid one through amino acid twenty of the HJ loop cyclic AMP dependent protein kinase and protein kinase C.

FIGS. 3A and 3B are a Table illustrating the amino acid sequence of the HJ loop of the serine/threonine kinases RAF (SEQ ID NO.: 1), cyclic AMP dependent protein kinase (CAPK) (SEQ ID NO.: 2), protein kinase C (PKC) (SEQ ID NO.: 3), the G-receptor coupled protein kinases β2-adrenergic receptor kinases 1 and 2 (bARK1.2) (SEQ ID NO.: 4), calmodulin dependent kinase (CaMK)(SEQ ID NO.: 5), polo kinases (SEQ ID NO.: 6), Akt/PKB (SEQ ID NO.: 7) and the G-protein coupled receptor kinases GRK1 (SEQ ID NO.: 8), GRK4 (SEQ ID NO.: 9), GRK5 (SEQ ID NO.: 10), GRK6 (SEQ ID NO.: 11) and GSK3 (SEQ ID NO.: 12). Also shown are examples of conservative substitutions in these amino acid sequences. An "*" indicates an aliphatic, substituted aliphatic, benzylic, substituted benzylic, aromatic or substituted aromatic ester of glutamic acid or aspartic acid.

FIG. 4 is a Table illustrating the sequences of the peptides HJ-38 (SEQ ID NO.: 13), J-41 (SEQ ID NO.: 14), J-42 (SEQ ID NO.: 15), J-43 (SEQ ID NO.: 16), J-43.1 (SEQ ID NO.: 17), J-45 (SEQ ID NO.: 18), J-46 (SEQ ID NO.: 19), J-47 (SEQ ID NO.: 20), J-48 (SEQ ID NO.: 21) and J-29 (SEQ ID NO.: 22). All peptides are N-acetylated and C-amidated. "E!" indicates a benzyl ester of glutamic acid.

FIG. 6A-6D are a Table showing the sequences of exemplary peptide derivatives of the present invention and the serine/threonine kinases from whose HJ loop they are derived. The peptide derivatives shown in FIG. 6 are K095H101 (SEQ ID NO.: 23); K048H101 (SEQ ID NO.: 24); K098H101 (SEQ ID NO.: 25); K099H101 (SEQ ID NO.: 26); K093H101 (SEQ ID NO.: 27); K014H101 (SEQ ID NO.: 28); K004H001 (SEQ ID NO.: 29); K004H002 (SEQ ID NO.: 30); K049H101 (SEQ ID NO.: 31); H050H101 (SEQ ID NO.: 32); K088H001 (SEQ ID NO.: 33); K088H101 (SEQ ID NO.: 34); K088H103 (SEQ ID NO.: 35); K088H104 (SEQ ID NO.: 36); K092H001 (SEQ ID NO.: 37); K018H101 (SEQ ID NO.: 38); K087H001 (SEQ ID NO.: 39); K087H101 (SEQ ID NO.: 40); K087H102 (SEQ ID NO.: 41); K087H103 (SEQ ID NO.: 42); K090H101 (SEQ ID NO.: 43); K091H001 (SEQ ID NO.: 44); K091H101 (SEQ ID NO.: 45); K107H001 (SEQ ID NO.: 46); K107H101 (SEQ ID NO.: 47); K107H102 (SEQ ID NO.: 48); K045H101 (SEQ ID NO.: 49); K045H102 (SEQ ID NO.: 50); K008H001 (SEQ ID NO.: 51); K008H101 (SEQ ID NO.: 52); K008H102 (SEQ ID NO.: 53); K008H103 (SEQ ID NO.: 54); K035H001 (SEQ ID NO.: 55); K035H101 (SEQ ID NO.: 56); K038H101 (SEQ ID NO.: 57); K038H102 (SEQ ID NO.: 58); K003H103 (SEQ ID NO.: 59); K003H104 (SEQ ID NO.: 60); K001H102 (SEQ ID NO.: 61); K001H103 (SEQ ID NO.: 62). Also shown in the Table are the sequences of peptide K014H010 (SEQ ID NO.: 63) which is C-amidated. The Table also illustrates peptides K014H111 (SEQ ID NO.: 64); K024H101 (SEQ ID NO.: 65); K048H901 (SEQ ID NO.: 66); K098H901 (SEQ ID NO.: 67); and K107H901 (SEQ ID NO.: 68). The N-terminal amino acids of these latter peptides are N-stearylated or N-myristylated. Their C-terminal is amidated.

Figure 5:
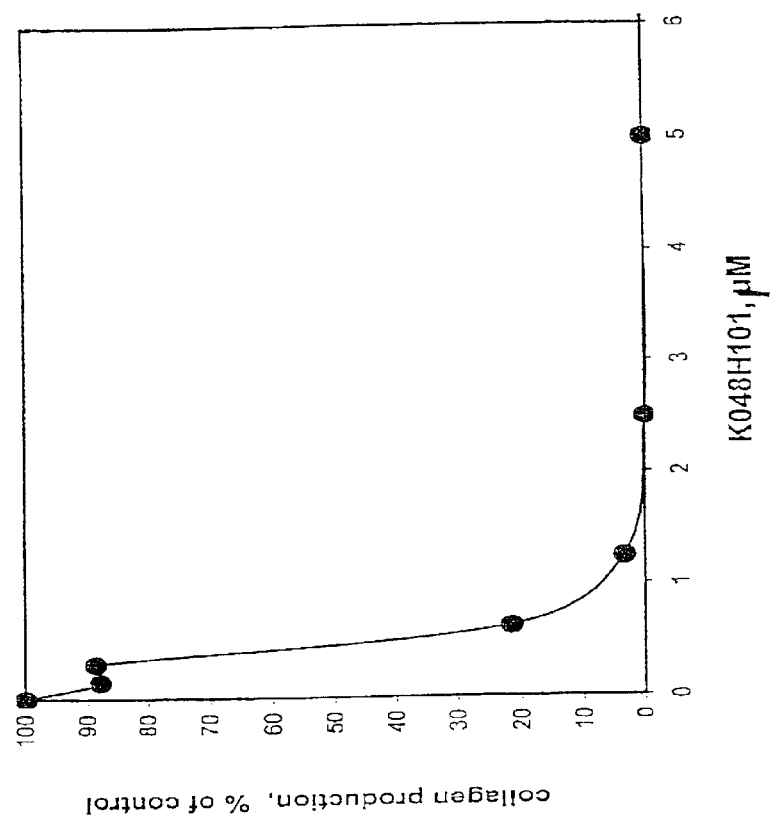
FIG. 5 is a graph showing the percent inhibition of collagen production in fetal lung fibroblasts in the presence of increasing concentrations (μM) of K048H101 (SEQ ID NO.: 24) relative to control. K048H101 is a peptide derivative of the HJ loop of the serine/threonine kinase ALK1.

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

A serine/threonine kinase (hereinafter "STK") is an intracellular or membrane bound protein which uses the gamma phosphate of ATP or GTP to generate phosphate monoesters on the hydroxyl group of a serine or threonine residue. STKs have homologous "kinase domains" or "catalytic domains" which carry out this phosphorylation. Based on a comparison of a large number of protein kinases, it is now known that the kinase domain of protein kinases, including STKs, can be divided into twelve subdomains, which are regions generally uninterrupted by large amino acid insertions and contain characteristic patterns of conserved residues (Hanks and Hunter, "The Eukaryotic Protein Kinase Superfamily", in Hardie and Hanks (ed.), *The Protein Kinase Facts Book, Volume* 1, Academic Press, Chapter 2, 1995. These subdomains are referred to as Subdomain I through Subdomain XII.

The "HJ loop" referred to herein is found within the kinase domain of STKs between the middle of Subdomain IX and the middle of Subdomain X. Because of the high degree of homology found in the subdomains of different protein kinases, including STKs, the amino acid sequences of the domains of different STKs can be aligned. Thus, the HJ loop of a STK can be defined by reference to the amino acid sequence of a prototypical protein kinase, for example PKA-Cα, and can be said to correspond to a contiguous sequence of about twenty amino acid residues found between about amino acid 229 and 248 of PKA-Cα.

A second definition of the HJ loop of a STK, which is complementary to the definition provided in the proceeding paragraph, can be made by reference to the three dimensional structure of the kinase domain of STKs. The kinase domain of STKs has been found to contain at least nine alpha helices, referred to as helix A through helix I (Tabor et al, *Phil. Trans. R. Soc. Lond. B* 340:315 (1993), Mohammadi et al., *Cell* 86:577 (1996) and Hubbard et al., *Nature* 372:746 (1994)). The HJ loop is a contiguous sequence of about twenty amino acids beginning within the F helix about five amino acids residues from the N-terminus of the F helix and extending about five amino acid residues into the G helix.

Optionally, the C-terminus or the N-terminus of the peptides of the present invention, or both, can be substituted with a carboxylic acid protecting group or an amine protecting group, respectively. Suitable protecting groups are described in Green and Wuts, *"Protecting Groups in Organic Synthesis"*, John Wiley and Sons, Chapters 5 and 7, 1991, the teachings of which are incorporated herein by reference. Preferred protecting groups are those which facilitate transport of the peptide into a cell, for example, by reducing the hydrophilicity and increasing the lipophilicity of the peptide. Examples of N-terminal protecting groups include acyl groups (—CO—$R_1$) and alkoxy carbonyl or aryloxy carbonyl groups (—CO—O—$R_1$), wherein $R_1$ is an aliphatic, substituted aliphatic, benzyl, substituted benzyl, aromatic or a substituted aromatic group. Specific examples of acyl groups include acetyl, (ethyl)-CO—, n-propyl-CO—, iso-propyl-CO—, n-butyl-CO—, sec-butyl-CO—, t-butyl-CO—, phenyl-CO—, substituted phenyl-CO—, benzyl-CO— and (substituted benzyl)-CO—. Examples of alkoxy carbonyl and aryloxy carbonyl groups include $CH_3$—O—CO—, (ethyl)-O—CO—, n-propyl-O—CO—, iso-propyl-O—CO—, n-butyl-O—CO—, sec-butyl-O—CO—, t-butyl-O—CO—, phenyl-O—CO—, substituted phenyl-O—CO— and benzyl-O—CO—, (substituted benzyl)-O—CO—. In a preferred embodiment of the invention, the peptides have an N-terminal amino acid which is a myristyl- or stearyl-substituted glycine. The carboxyl group at the C-terminus can be protected, for example, as an an amide (i.e., the hydroxyl group at the C-terminus is replaced with—$NH_2$, —$NHR_2$ and —$NR_2R_3$) or ester (i.e. the hydroxyl group at the C-terminus is replaced with —$OR_2$). $R_2$ and $R_3$ are independently an aliphatic, substituted aliphatic, benzyl, substituted benzyl, aryl or a substituted aryl group. In addition, taken together with the nitrogen atom, $R_2$ and $R_3$ can form a C4 to C8 heterocyclic ring with from about 0–2 additional heteroatoms such as nitrogen, oxygen or sulfur. Examples of suitable heterocyclic rings include piperidinyl, pyrrolidinyl, morpholino, thiomorpholino or piperazinyl. Examples of C-terminal protecting groups include —$NH_2$, —$NHCH_3$, —$N(CH_3)_2$, —NH(ethyl), —N(ethyl)$_2$, —N(methyl)(ethyl), —NH(benzyl), —N(C1–C4 alkyl)(benzyl), —NH(phenyl), —N(C1–C4 alkyl)(phenyl), —$OCH_3$, —O-(ethyl), —O-(n-propyl), —O-(n-butyl), —O-(iso-propyl), —O-(sec-butyl), —O-(t-butyl), —O-benzyl and —O-phenyl.

A "peptide derivative of the HJ loop" includes a peptide having the amino acid sequence of the HJ loop. A "peptide derivative of the HJ loop" also includes, for example, a subsequence of the HJ loop of the STK. A subsequence is a contiguous sequence of from about five to about twenty amino acids or amino acid residues found within a larger sequence. Thus, a subsequence of the HJ loop is a contiguous sequence of from about five to about twenty amino acids or amino acid residues found within the HJ loop. A subsequence of the HJ loop can also be referred to as a "fragment" of the HJ loop.

A "peptide derivative" also includes a peptide having a "modified sequence" in which one or more amino acids in the original sequence or subsequence have been substituted with a naturally occurring amino acid or amino acid analog (also referred to as a "modified amino acid"). In one aspect of the present invention, the peptide derivative has a sequence corresponding to a subsequence of the HJ loop of a STK, with the proviso that any one amino acid residue in the peptide derivative can differ from the corresponding amino acid residue in the subsequence. For example, if the subsequence is $[AA_1]-[AA_2]-AA_3]-[AA_4]-[AA_5]$, then the peptide derivative can be $[AA_1']-[AA_2]-[AA_3]-[AA_4]-[AA_5]$, $[AA_1]-[AA_2']-[AA_3]-[AA_4]-[AA_5]$, $[AA_1]-[AA_2]-[AA_3']-[AA_4]-[AA_5]$, $[AA_1]-[AA_2]-[AA_3]-[AA_4']-[AA_5]$ and $[AA_1]-[AA_2]-[AA_3]-[AA_4]-[AA_5']$, wherein $[AA']$ is a naturally occurring or modified amino acid different from $[AA]$. In another aspect of the present invention, the peptide derivative has a sequence corresponding to a subsequence of the HJ loop of an STK, with the proviso that any two amino acid residues in the peptide derivative can differ from the corresponding amino acid residue in the subsequence.

An "amino acid residue" is a moiety found within a peptide and is represented by —NH—CHR—CO—, wherein R is the side chain of a naturally occurring amino acid. When referring to a moiety found within a peptide, the terms "amino acid residue" and "amino acid" are used interchangeably in this application. An "amino acid residue analog" includes D or L residues having the following formula: —NH—CHR—CO—, wherein R is an aliphatic group, a substituted aliphatic group, a benzyl group, a substituted benzyl group, an aromatic group or a substituted aromatic group and wherein R does not correspond to the side chain of a naturally-occurring amino acid. When referring to a moiety found within a peptide, the terms "amino acid residue analog" and "amino acid analog" are used interchangeably in this application.

As used herein, aliphatic groups include straight chained, branched or cyclic C1–C8 hydrocarbons which are completely saturated, which contain one or two heteroatoms such as nitrogen, oxygen or sulfur and/or which contain one or more units of unsaturation. Aromatic groups include carbocyclic aromatic groups such as phenyl and naphthyl and heterocyclic aromatic groups such as imidazolyl, indolyl, thienyl, furanyl, pyridyl, pyranyl, pyranyl, oxazolyl, benzothienyl, benzofuranyl, quinolinyl, isoquinolinyl and acridintyl.

Suitable substituents on an aliphatic, aromatic or benzyl group include —OH, halogen (—Br, —Cl, —I and —F) —O(aliphatic, substituted aliphatic, benzyl, substituted benzyl, aryl or substituted aryl group), —CN, —NO$_2$, —COOH, —NH$_2$, —NH(aliphatic group, substituted aliphatic, benzyl, substituted benzyl, aryl or substituted aryl group), —N(aliphatic group, substituted aliphatic, benzyl, substituted benzyl, aryl or substituted aryl group)$_2$, —COO (aliphatic group, substituted aliphatic, benzyl, substituted benzyl, aryl or substituted aryl group), —CONH$_2$, —CONH (aliphatic, substituted aliphatic group, benzyl, substituted benzyl, aryl or substituted aryl group)), —SH, —S(aliphatic, substituted aliphatic, benzyl, substituted benzyl, aromatic or substituted aromatic group) and —NH—C(=NH)—NH$_2$. A substituted benzylic or aromatic group can also have an aliphatic or substituted aliphatic group as a substituent. A substituted aliphatic group can also have a benzyl, substituted benzyl, aryl or substituted aryl group as a substituent. A substituted aliphatic, substituted aromatic or substituted benzyl group can have one or more substituents.

Suitable substitutions for amino acid residues in the sequence of an HJ loop or a subsequence of an HJ loop include conservative substitutions which result in peptide derivatives which modulate the activity of a STK. A "conservative substitution" is a substitution in which the substituting amino acid (naturally occurring or modified) has about the same size and electronic properties as the amino acid being substituted. Thus, the substituting amino acid would have the same or a similar functional group in the side chain as the original amino acid.

A "conservative substitution" also refers to utilizing a substituting amino acid which is identical to the amino acid being substituted except that a functional group in the side chain is functionalized with a suitable protecting group. Suitable protecting groups are described in Green and Wuts, "Protecting Groups in Organic Synthesis", John Wiley and Sons, Chapters 5 and 7, 1991, the teachings of which are incorporated herein by reference. As with N-terminal and C-terminal protecting group, preferred protecting groups are those which facilitate transport of the peptide into a cell, for example, by reducing the hydrophilicity and increasing the lipophilicity of the peptide, and which can be cleaved in vivo, either by hydrolysis or enzymatically, inside the cell. (Ditter et al., *J Pharm. Sci.* 57:783 (1968); Ditter et al., *J. Pharm. Sci.* 57:828 (1968); Ditter et al., *J Pharm. Sci.* 58:557 (1969); King et al., *Biochemistry* 26:2294 (1987); Lindberg et al., *Drug Metabolism and Disposition* 17:311 (1989); and Tunek et al., *Biochem. Pharm.* 37:3867 (1988), Anderson et al., *Arch. Biochem. Biophys.* 239:538 (1985) and Singhal et al., *FASEB J* 1:220 (1987)). Hydroxyl protecting groups include esters, carbonates and carbamate protecting groups. Amine protecting groups include alkoxy and aryloxy carbonyl groups, as described above for N-terminal protecting groups. Carboxylic acid protecting groups include aliphatic, benzylic and aryl esters esters, as described above for C-terminal protecting groups. In one embodiment, the carboxylic acid group in the side chain of one or more glutamic acid or aspartic acid residue in a peptide of the present invention is protected, preferably with as a methyl, ethyl, benzyl or substituted benzyl ester, more preferably as a benzyl ester.

Provided below are groups of naturally occurring and modified amino acids in which each amino acid in a group has similar electronic and steric properties. Thus, a conservative substitution can be made by substituting an amino acid with another amino acid from the same group. It is to be understood that these groups are non-limiting, i.e. that there are additional modified amino acids which could be included in each group.

Group I includes leucine, isoleucine, valine, methionine, serine, cysteine, threonine and modified amino acids having the following side chains: ethyl, n-butyl, —CH$_2$CH$_2$OH, —CH$_2$CH$_2$CH$_2$OH, —CH$_2$CHOHCH$_3$ and —CH$_2$SCH$_3$. Preferably, Group I includes leucine, isoleucine, valine and methionine.

Group II includes glycine, alanine, valine, serine, cysteine, threonine and a modified amino acid having an ethyl side chain. Preferably, Group II includes glycine and alanine.

Group III includes phenylalanine, phenylglycine, tyrosine, tryptophan, cyclohexylmethyl, and modified amino residues having substituted benzyl or phenyl side chains. Preferred substituents include one or more of the following: halogen, methyl, ethyl, nitro, methoxy, ethoxy and —CN. Preferably, Group m includes phenylalanine, tyrosine and tryptophan.

Group IV includes glutamic acid, aspartic acid, a substituted or ubsubstituted aliphatic, aromatic or benzylic ester of glutamic or aspartic acid (e.g., methyl, ethyl, n-propyl iso-propyl, cyclohexyl, benzyl or substituted benzyl), glutamate, asparagine, CO—NH-alkylated glutamate or asparagine (e.g., methyl, ethyl, n-propyl and iso-propyl) and modified amino acids having the side chain —$(CH_2)_3$—COOH, an ester thereof (substituted or unsubstituted aliphatic, aromatic or benzylic ester), an amide thereof and a substituted or unsubstituted N-alkylated amide thereof. Preferably, Group IV includes glutamic acid, aspartic acid, methyl aspartate, ethyl asparatate, benzyl asparate and methyl glutamate, ethyl glutamate and benzyl glutamate.

Group V includes histidine, lysine, arginine, N-nitroarginine, β-cycloarginine, γ-hydroxyarginine, N-amidinocitruline and 2-amino-4-guanidinobutanoic acid, homologs of lysine, homologs of arginine and ornithine. Preferably, Group V includes histidine, lysine, arginine, and ornithine. A homolog of an amino acid includes from 1 to about 3 additional methylene units in the side chain.

Group VI includes serine, theronine, cysteine and modified amino acids having C1–C5 straight or branched alkyl side chains substituted with —OH or —SH. Preferably, Group VI includes serine, cysteine or threonine.

In another aspect, suitable substitutions for amino acid residues in the sequence of an HJ loop or a subsequence of an HJ loop include "severe" substitutions which result in peptide derivatives which modulate the activity of a STK. Severe substitutions which result in peptide derivatives that modulate the activity of a STK are much more likely to be possible in positions which are not highly conserved throughout the family of serine/threonine kinases than at positions which are highly conserved. FIG. 1 shows the consensus sequence of the about first ten amino acids of the HJ loop of STKs. FIG. 2 shows the consensus sequence of the about twenty amino acids of the HJ loop of cyclic AMP dependent kinase and protein kinase C. Positions which are highly conserved among the STK family and the conserved amino acids generally found in those positions have been indicated. Positions which are not as highly conserved among the STK family are indicated with an "X". Because D-amino acids have a hydrogen at a position identical to the glycine hydrogen side-chain, D-amino acids or their analogs can be substituted for the glycine at position 6 in FIG. 1 or at positions 6 and 12 in FIG. 2.

A "severe substitution" is a substitution in which the substituting amino acid (naturally occurring or modified) has significantly different size and/or electronic properties compared with the amino acid being substituted. Thus, the side chain of the substituting amino acid can be significantly larger (or smaller) than the side chain of the amino acid being substituted and/or can have functional groups with significantly different electronic properties than the amino acid being substituted. Examples of severe substitutions of this type include the substitution of phenylalanine or cyclohexylmethyl glycine for alanine, isoleucine for glycine, a D amino acid for the corresponding L amino acid or —NH—CH[(—$CH_2)_5$—COOH]—CO— for aspartic acid. Alternatively, a functional group may be added to the side chain, deleted from the side chain or exchanged with another functional group. Examples of severe substitutions of this type include adding an amine or hydroxyl, carboxylic acid to the aliphatic side chain of valine, leucine or isoleucine, exchanging the carboxylic acid in the side chain of aspartic acid or glutamic acid with an amine or deleting the amine group in the side chain of lysine or ornithine. In yet another alternative, the side chain of the substituting amino acid can have significantly different steric and electronic properties than the functional group of the amino acid being substituted. Examples of such modifications include tryptophan for glycine, lysine for aspartic acid and —$(CH_2)_4$COOH for the side chain of serine. These examples are not meant to be limiting.

Examples of STKs whose activity can be modulated by peptide and peptide derivatives, as described herein, include, but are not limited to, STKs belonging to the following STK families: polo family (Glover et al., *J Cell Biol.*, 135:1681 (1996)), Raf, mitogen-activated protein kinases (MAP kinases), Akt/PKB (Frank et al., *Cell* 88.435 (1997) and Hemmings et al., *Science* 275:628 (1997)) and G protein-coupled receptor kinases. Other suitable STKs include cyclic AMP (cAMP) dependent protein kinase, protein kinase C, calmodulin dependent kinase, glycogen synthase kinase-3 (GSK3) and cyclic GMP (cGMP) dependent protein kinase.

Suitable members of the polo family include, but are not limited to, Plk, Snk and Sak. Suitable members of the Raf family include, but are not limited to, Raf-1, A-Raf and B-Raf. Suitable G-protein dependent kinases include, but are not limited to, β-adrenergic receptor kinases 1 and 2, rhodopsi kinase (GRK1), GRK4, GRK5 and GRK6. Suitable MAP kinases include, but are not limited to MAPK, MAPKK and MAPKKK. Also included are the protein kinase C isoforms, which include, but are not limited to, isoforms designated as α, $β_{I/II}$, γ, δ, ε, η(L), θ, μ, ξ, τ and λ.

The present invention includes peptides having amino acids sequences corresponding to the sequence found in the HJ loop of STKs, subsequences thereof and modified subsequences thereof. Examples of suitable subsequences include, but are not limited to, sequences corresponding to $[AA]_1$ through $[AA]_{20}$, $[AA]_3$ through $[AA]_{10}$, $[AA]_7$ through $[AA]_{14}$, $[AA]_{11}$ through $[AA]_{18}$, $[AA]_3$ through $[AA]_{14}$, $[AA]_7$ through $[AA]_{18}$ and $[AA]_3$ through $[AA]_{18}$ of the HJ loop of a STK, and subsequences thereof. FIG. 3 shows the sequences of the HJ loop of the following STKs: RAF, cyclic AMP dependent kinase, protein kinase C, the G-protein-coupled receptor kinases βARK 1 and 2 and GRK1, GRK4, GRK5 and GRK6, calmodulin dependent kinase, polo, Akt/PKB and GSK3.

FIG. 3 also provides a numbering scheme for the amino acid sequence in an loop. The amino acid at the N-terminus of the HJ loop is at position 1 and can be referred to as "$[AA]_1$". The next amino acid in the sequence, referred to as "$[AA]_2$", is at position 2 and is followed by amino acids $[AA]_3$ through $[AA]_{20}$, which are at positions 3–20. Thus, a peptide 20-mer with an amino acid sequence $[AA]_1$ through $[AA]_{20}$ includes the twenty amino acids in the HJ loop. A peptide derivative of the HJ loop with an amino acid sequence $[AA]_3$ through $[AA]_{10}$, as recited in the preceeding paragraph, includes the third amino acid through the tenth amino acid in said HJ loop.

The present invention also includes peptides having amino acid sequences corresponding to a modified sequence or subsequence of the HJ loop of STKs and which modulate the activity of STKs including RAF, cyclic AMP dependent kinase, protein kinase C, the G-protein-coupled receptor kinases βARK 1, βARK2, GRK1 and GRKs4–6, calmodulin dependent kinase and polo. In one aspect, one, two or more of the amino acids in the sequence or subsequence are modified with conservative substitutions; the substitutions can be in consensus positions, in non-consensus positions or in both. In another aspect, one, two or more of the amino acids in the sequence or subsequence are modified with severe substitutions; the substitutions are preferably in nonconsensus positions. Also included are the substitution of conserved glycine residues (e.g., position 6 in FIG. 1 or positions 6 and 12 in FIG. 2) with D-amino acid residues or analogs thereof. FIG. 3 also provides examples of conservative amino acid substitutions for the HJ loop of RAF, cyclic AMP dependent kinase, protein kinase C, the G-protein-coupled receptor kinases βARK1, βARK2, GRK1 and GRKs4–6, calmodulin dependent kinase, polo, Akt/PKB and GSK3.

Specific examples of peptide derivatives of the present invention include peptides HJ-38 (SEQ ID NO.: 13), J-41 (SEQ ID NO.: 14), J-42 (SEQ ID NO.: 15), J-43 (SEQ ID NO.: 16), J-43.1 (SEQ ID NO.: 17), J-45 (SEQ ID NO.: 18), J-46 (SEQ ID NO.: 19), J-47 (SEQ ID NO.: 20), J-48 (SEQ ID NO.: 21) and J-29 (SEQ ID NO.: 22), as well as peptides the sequences of which are shown in FIG. 4. Additional specific sequences shown in FIGS. 6A–6D. The N-terminus and/or C-terminus of these peptides can be modified, as described above. For example, the N-terminal of most of these peptides is acetylated, stearylated or myristylated and the C-terminal is amidated. Other protecting groups for amides and carboxylic acids can be used, as described above. Optionally, one or both protecting groups can be omitted. The peptides maybe linear or cyclic.

Also included are peptides having the sequence of HJ-38 (SEQ ID NO.: 13), J-41 (SEQ ID NO.: 14), J-42 (SEQ ID NO.: 15), J-43 (SEQ ID NO.: 16), J-43.1 (SEQ ID NO.: 17), J-45 (SEQ ID NO.: 18), J-46 (SEQ ID NO.: 19), J-47 (SEQ ID NO.: 20), J-48 (SEQ ID NO.: 21), J-29 (SEQ ID NO.: 22), as well as sequences shown in FIGS. 6A–6D, with the proviso that any one of the amino residues in the peptide can vary, being any naturally occurring amino acid or analog thereof. The present invention also includes peptides having the sequences discussed above with the proviso that any two of the amino residues in the peptide can vary, being any naturally occurring amino acid or analog thereof.

The present invention also includes cyclic peptides having amino acids sequences corresponding to a modified sequence or subsequence of the HJ loop of STKs and which modulate the activity of STKs.

A "cyclic peptide" refers, for example, to a peptide or peptide derivative in which a ring is formed by a peptide bond between the nitrogen atom at the N-terminus and the carbonyl carbon at the C-terminus.

"Cyclized" also refers to forming a ring by a covalent bond between the nitrogen at the N-terminus of the compound and the side chain of a suitable amino acid in the peptide, preferably the C-terminal amino acid. For example, an amide can be formed between the nitrogen atom at the N-terminus and the carbonyl carbon in the side chain of aspartic acid or glutamic acid. Alternatively, the peptide or peptide derivative can be cyclized by forming a covalent bond between the carbonyl at the C-terminus of the compound and the side chain of a suitable amino acid in the peptide, preferably the N-terminal amino acid. For example, an amide can be formed between the carbonyl carbon at the C-terminus and the amino nitrogen atom in the side chain lysine or ornithine; an ester can be formed between the carbonyl carbon at the C-terminus and the hydroxyl oxygen atom in the side chain of serine or threonine.

"Cyclized" also refers to forming a ring by a covalent bond between the side chains of two suitable amino acids in the peptide, preferably the terminal amino acids. For example, a disulfide can be formed between the sulfur atoms in the side chains of two cysteines. Alternatively, an ester can be formed between the carbonyl carbon in the side chain of, for example, glutamic acid or aspartic acid, and the oxygen atom in the side chain of, for example, serine or threonine. An amide can be formed between the carbonyl carbon in the side chain of, for example, glutamic acid or aspartic acid, and the amino nitrogen in side chain of, for example, lysine or ornithine.

In addition, a peptide or peptide derivative can be cyclized with a linking group between the two termini, between one terminus and the side chain of an amino acid in the peptide or peptide derivative, or between the side chains to two amino acids in the peptide or peptide derivative. Suitable linking groups are disclosed in Lobl et al, WO 92/00995 and Chiang et al., WO 94/15958, the teachings of which are incorporated into this application by reference.

Suitable substitutions in the original amino acid sequence or subsequence are those which result in a peptide derivative, as defined above, which modulates the activity of a STK. The activity of a STK is "modulated" when the activity of the STK is increased or decreased. An increase or decrease in the activity of a STK can be detected by assessing in vitro the extent of phosphorylation of a protein substrate of the STK being tested or by a corresponding modulation, increase or decrease, in a cellular activity or function which is under the control of the STK. Examples of these cellular functions include cell proliferation, cell differentiation, cell morphology, cell survival or apoptosis, cell response to external stimuli, gene expression, lipid metabolism, glycogen metabolism and mitosis.

It can be readily determined whether a peptide or peptide derivative modulates the activity of a STK by providing cells which have one or more cellular activities controlled by a STK. The cells are incubated with the peptide or peptide derivative to produce a test mixture under conditions suitable for assessing activity of the serine/threonine kinase. The activity of the STK is assessed and compared with a suitable control, e.g., the activity of the same cells incubated under the same conditions in the absence of the peptide or peptide derivative. A greater or lesser activity of the STK in the test mixture compared with the control indicates that the test peptide or peptide derivative modulates the activity of said STK.

Suitable cells for the assay include normal cells which express a membrane bound or intracellular STK, cells which have been genetically engineered to express a STK, malignant cells expressing a STK or immortalized cells which express a STK.

Conditions suitable for assessing STK activity include conditions suitable for assessing activity of a cellular activity or function under control of the STK. Generally, a cellular activity or function can be assessed when the cells are exposed to conditions suitable for cell growth, including a suitable temperature (for example, between about 30° C. to about 42° C.) and the presence of the suitable concentrations of nutrients in the medium (e.g., amino acids, vitamins, growth factors).

In another aspect, the activity of certain STK (e.g., Atk/PKB, Dudek et al., Science 275:661 (1997)) can be evaluated by growing the cells under serum deprivation conditions. Cells are typically grown in culture in the presence of a serum such as bovine serum, horse serum or fetal calf serum. Many cells, for example, nerve cells such as PC-12 cells, generally do not survive when there is insufficient serum. The use of insufficient serum to culture cells is referred to as "serum deprivation conditions" and includes, for example, from 0% to about 4% serum. STK activity is determined by the extent to which a peptide or peptide derivative can protect cells, e.g., neuronal cells, from the consequences of serum deprivation. Specific conditions are provided in Dudek et al., and in Example 4 of co-pending and concurrently filed application entitled "SHORT PEPTIDES WHICH SELECTIVELY MODULATE INTRACELLULAR SIGNALLING" U.S. patent application Ser. No. 08/861,153, filed on May 21, 1997, now U.S. Pat. No. 6,723,694, the teachings of which are incorporated herein by reference.

Generally, the activity of the STK in the test mixture is assessed by making a quantitative measure of the cellular activity which the STK controls. The cellular activity can be, for example, cell proliferation. Examples of cells in which proliferation is controlled by an STK include endothelial cells such as bovine aortic cells, mouse MSI cells or mouse SVR cells (see Arbiser et al., *Proc. Nati. Acad. Sci. USA* 94:861 (1997)), vascular smooth muscle cells, and malignant cells of various tissues such as breast cancer, lung cancer, colon cancer, prostrate cancer, melanoma. STK activity is assessed by measuring cellular proliferation, for example, by comparing the number of cells present after a given period of time with the number of cells originally present. STKs involved in cell proliferation are members of the polo family, Taf or Atk/PKB. If cells are being used in which the STK controls the cell differentiation (e.g., preadipocytes such as 3T3-L1 expressing STKs Akt/PKB, GSK3 and protein kinase A—see Kohn et al., *J. Biol. Chem.* 272:31372 (1996)), activity is assessed by measuring the degree of differentiation. Activity can be assessed by changes in the metabolic activity of cells such as primary adipocytes, hepatocytes and fibroblasts by measuring changes in glucose uptake, lipogenesis, or glycogen metabolism (see, for example, Weise et al., *J. Biol. Chem.* 270:3442 (1995)). Activity can also be assessed by the extent to which the gene expression, cell morphology or cellular phenotype is altered (e.g., the degree to which cell shape is altered or the degree to which the cells assume a spindle-like structure). One example of a change in cellular morphology is reported in the U.S. Pat. No. 6,723,674, entitled "SHORT PEPTIDES WHICH SELECTIVELY MODULATE INTRACELLULAR SIGNALLING", which discloses that certain peptide derivatives of the HJ loop of protein tyrosine kinases can cause vascular smooth muscle cells to become elongated and assume a spindle-like shape.

Specific examples of conditions suitable for determining the activity of STKs by assessing cell proliferation are provided in Example 2.

It is to be understood that the assay described hereinabove for determining whether a peptide or peptide derivative modulates a cellular activity or function under the control of a STK can be performed with cells other than those specifically described herein. STKs not yet discovered or STKs whose function is not yet known can also be used in this assay, once it has been determined which cellular functions or activities they control. These STKs are also within the scope of the present invention.

The present invention is also directed to a method of modulating the activity of a serine/threonine kinase in a subject. A "subject" is preferably a human, but can also be animals in need of treatment, e.g., veterinary animals (e.g., dogs, cats, and the like), farm animals (e.g., cows, pigs, horses and the like) and laboratory animals (e.g., rats, mice, guinea pigs and the like).

The activity of a STK in a subject can be modulated for the purpose of treating diseases which are caused by over activity or under activity of STKs. For example, MAP kinases (Seger and Krebs, *FASEB J* 9:726 (1995)) and cyclin dependent protein kinases ("Molecular Biology of the Cell," Alberts, Bray, Lewis, Raff, Roberts and Watson, eds. Chapter 5, (Garland Publishing, Inc.), (1994)), are central components of the cell-division cycle control system in eukaryotic cells. Other STKs, for example, protein kinase C, Raf kinases (Nishizuka, *The FASEB Journal* 9:484 (1995), Locric, et al, *Oncogene* 12:1109 (1996) and Laird et al., *J Biol. Chem.* 270:26,742 (1995)) and G protein-coupled receptors (Lange-Carter, et al, *Science* 260:315 (1993)), are, in turn, involved in the control of MAP kinases or are activated during mitosis. The G protein-coupled receptor kinases (GRKs), on the other hand, desensitize the receptors and are thereby involved in the regulation of various hormonal responses (Freedman and Lefkowitz, *Recent Prog. Hormon. Res.* 51:319 (1996). Activation of Akt/PKB is implicated in the inhibition of apoptosis, i.e., programmed cell death (Frank et al., *Cell* 88:435 (1997) and Hemmings *Science* 275:628 (1997)). Peptides and peptide derivatives of the present invention which modulate the activity of these enzymes can be used to treat cancer in a subject when administered to the subject in a therapeutically effective amount.

c-AMP dependent kinase, GSK3 and Akt/PKB are involved in the control of glycogen metabolism. Peptide and peptide derivatives of the present invention which modulate the activity of cAMP dependent kinase can be used to treat Type II diabetes and hemorrhagic shock in a subject when administered to the subject in a therapeutically effective amount. cAMP derivatives have also been reported to inhibit the growth of human cancer cells (Katsros et al., *FEBS Lett.* 223:97 (1987)), indicating that inhibitors of cAMP dependent kinases can also be useful in the treatment of cancer.

Raf kinases are involved in the control of lipid metabolism. Peptide and peptide derivatives of the present invention which modulate the activity of Raf kinases can be used to treat obesity in a subject when administered to the subject in a therapeutically effective amount.

Agents which modulate the activity of protein kinase C can be used to treat a wide variety of disease conditions, including cardiovascular diseases (e.g., thrombosis, atherosclerosis, arteriosclerosis, cardiac hypertrophy, ischemia, reperfusion injury and hypertension), immunosuppresive and inflammatory disorders (e.g., asthma, psoriasis, systemic lupus erythematosus, diabetes mellitus, supression of organ transplant rejection, multiple sclerosis, inflammatory bowel disease and AIDS), central nervous system diseases (e.g., Alzheimer's disease, stroke and trauma), septic shock based on protein kinase C activation and ischemia induced renal failure (Nambi, WO 93/16703, Bradshaw, et al., *Agents Action* 38:135 (1993) and Birchall et al., *The J. Pharm. and Exper. Therapeut.* 2:922 (1994)). Peptide and peptide derivatives of the present invention which modulate the activity of protein kinase C can be used to treat these diseases in a subject when administered to the subject in a therapeutically effective amount.

Phosphorylation by G-protein receptor kinases are known (Freedman and Lefkowitz, *Recent Prog. Hormon. Res.* 51:319 (1996)) to result in receptor desensitization, thereby extending the extending the duration of hormonal effects of, for example, adrenalin. Thus, agents which modulate the activity of G-protein receptor kinases have potential in the treatment of disease resulting from a lower bioavailability of the corresponding ligand, such as dopamine. Inhibitors of calmodulin dependent kinases have been reported to inhibit dopamine release (Nagatsu et al., *Biochem. Biophys. Research, Commun.* 143:1045 (1987)). Thus, agents which modulate the activity of G-protein receptor kinases and calmodulin receptor kinases are potentially useful in the treatment of diseases involving dysfunction of dopamine signalling, for example, Parkinson's Disease. Inhibitors of calmodulin dependent kinases have also been reported to relax arterial muscle (Saitoh et al, *J Bio. Chem.* 262:7796 (1987)) and therefore have potential in treating hypertension. Inhibition of GSK3 might increase the intracellular activity of the insulin receptor and thereby enhance glucose uptake and other related metobolic activities. Thus, agents which modulate the activity of GSK3 are potentially useful in the treatment of Type I and Type II diabetes.

Based on methods disclosed herein, peptides and peptide derivatives can be designed to modulate the activity of STKs whose HJ loop has been sequenced and whose cellular function is known. As a consequence, peptides and peptide derivatives can be designed to affect (increase or decrease) those cellular functions. It is possible that future research will reveal that certain disease conditions, whose underlying causes are presently unknown, are brought about by the overactivity or underactivity of cellular functions controlled by STKs. These diseases can be treated by administering peptides which are peptide derivatives of the HJ loop of the overactive or underactive STK. Suitable peptides and peptide derivatives can be identified by methods disclosed herein. These methods of treatment, peptides and peptide derivatives are encompassed within the scope of the present invention.

A "therapeutically effective amount" is the quantity of compound which results in an improved clinical outcome as a result of the treatment compared with a typical clinical outcome in the absence of the treatment. An "improved clinical outcome" includes a longer life expectancy for individuals with the disease as a result of the treatment. An "improved clinical outcome" can also result in the individual with the disease experiencing fewer symptoms or complications of the disease as a result of the treatment. With respect to cancer, an "improved clinical outcome" includes a longer life expectancy. It can also include slowing or arresting the rate of growth of a tumor, causing a shrinkage in the size of the tumor, a decreased rate of metastasis and/or improved quality of life (e.g., a decrease in physical discomfort or an increase in mobility).

With respect to diabetes, an improved clinical outcome refers to a longer life expectancy, a reduction in the complications of the disease (e.g., neuropathy, retinopathy, nephropathy and degeneration of blood vessels) and an improved quality of life, as described above.

With respect to obesity, an improved clinical outcome refers to increased weight reduction per calorie intake. It also refers to a decrease in the complications which are a consequence of obesity, for example heart disease such as arteriosclerosis and high blood pressure.

The amount of peptide or peptide derivative administered to the individual will depend on the type and severity of the disease and on the characteristics of the individual, such as general health, age, sex, body weight and tolerance to drugs. The skilled artisan will be able to determine appropriate dosages depending on these and other factors. Typically, a therapeutically effective amount of the peptide or peptide derivative can range from about 1 mg per day to about 1000 mg per day for an adult. Preferably, the dosage ranges from about 1 mg per day to about 100 mg per day.

The peptide and peptide derivatives of the present invention are preferably administered parenterally. Parenteral administration can include, for example, systemic administration, such as by intramuscular, intravenous, subcutaneous, or intraperitoneal injection. Peptides or peptide derivatives which resist proteolysis can be administered orally, for example, in capsules, suspensions or tablets.

The peptide or peptide derivative can be administered to the individual in conjunction with an acceptable pharmaceutical carrier as part of a pharmaceutical composition for treating the diseases discussed above. Suitable pharmaceutical carriers may contain inert ingredients which do not interact with the peptide or peptide derivative. Standard pharmaceutical formulation techniques may be employed such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., *Controlled Release of Biological Active Agents*, John Wiley and Sons, 1986).

The peptide and peptide derivatives of the present invention have many utilities other than for therapy. Some of these uses are discussed in the following paragraphs.

The HJ loop peptides of the present invention are derived from an array which is linear in the native protein. Therefore, they can be useful in the preparation of specific antibodies against STKs. Moreover, since the HJ-loop sequence is unique to each sub-family of STK, anti-HJ-loop antibodies can be specifically used to isolate distinct sub-families of STK.

Suitable antibodies can be raised against an HJ loop peptide by conjugating to a suitable carrier, such as keyhole limpet hemocyanin or serum albumin; polyclonal and monoclonal antibody production can be performed using any suitable technique. A variety of methods have been described (see e.g., Kohler et al., *Nature,* 256: 495–497 (1975) and *Eur. J. Immunol.* 6. 511–519 (1976); Milstein et al., *Nature* 266: 550–552 (1977); Koprowski et al., U.S. Pat. No. 4,172,124; Harlow, E. and D. Lane, 1988, *Antibodies: A Laboratory Manual,* (Cold Spring Harbor Laboratory: Cold Spring Harbor, N.Y.); *Current Protocols In Molecular Biology,* Vol. 2 (Supplement 27, Summer 1994), Ausubel, F. M. et al., Eds., (John Wiley & Sons: New York, N.Y.), Chapter 11, (1991)). Generally, a hybridoma can be produced by fusing a suitable immortal cell line (e.g., a myeloma cell line such as SP2/0) with antibody producing cells. The antibody producing cell, preferably those of the spleen or lymph nodes, can be obtained from animals immunized with the antigen of interest. The fused cells (hybridomas) can be isolated using selective culture conditions, and cloned by limiting dilution. Cells which produce antibodies with the desired specificity can be selected by a suitable assay (e.g., ELISA).

Antibodies, including monoclonal antibodies, against HJ loop peptides have a variety of uses. For example, those against or reactive with the protein from which the HJ peptides was derived, and preferably which bind specifically to said protein, can be used to identify and/or sort cells exhibiting that protein on the cell surface (e.g., by means of flourescence activated cell sorting or histological analyses).

Monoclonal antibodies specific for the protein can also be used to detect and/or quantitate the protein expressed on the surface of a cell or present in a sample (e.g., in an ELISA). Alternatively, the antibodies can be used to determine if an intracellular STK is present in the cytoplasm of the cell. A cleared lysate of the cell is generated (for example, by treating the cells with sodium hydroxide (0.2 N) and sodium dodecyl sulfate (1%), centrifugating and separating the supernatant from the pellet), and treated with anti-HJ loop antibody specific for the STK. The cleared lysate is then analzyed, for example, by Western blotting or immunoprecipitation for complexes between STK and antibody. Some STKs become membrane-bound or cytoskeleton-associated following stimulation. Anti-HJ-loop antibodies can be utilized for the study of the intracellular distribution (compartmentalization) of various subfamilies of STKs under various physiologigal conditions via the application of conventional immunocytochemistry such as immunofluoresence, immunoperoxidase technique and immunoelectron microscopy, in conjunction with the specific anti-HJ-loop antibody.

Antibodies reactive with the immunogen are also useful. For example, they can be used to detect and/or quantitate immunogen in a sample, or to purify immunogen (e.g., by immunoaffinity purification).

The HJ loop within STKs plays a key role in regulating the activity of STKs, as is evidenced by the fact that the peptides and peptide derivatives of the present invention have such a dramatic effect on the activity of STKs. The HJ loop peptides of the present invention can also be used to identify ligands which interact with the HJ-loops of specific STKs and which modulate the activity STKs. For example, an affinity column can be prepared to which a specific HJ-loop is covalently attached, directly or via a linker. This column, in turn, can be utilized for the isolation and identification of specific ligands which bind the HJ loop peptide and which will also likely bind the STK from which the HJ loop peptide was derived. The ligand can then be eluted from the column, characterized and tested for its ability modulate STK function.

Protein tyrosine kinases are another class of protein kinases. These proteins occur as membrane-bound receptors, which participate in transmembrane signaling, or as intracellular proteins which take part in signal transduction within the cell, including signal transduction to the nucleus. Binding of a ligand results in signal transduction, initiated by the phosphorylation of tyrosine residues of intracellular proteins by the kinase. As with STKs, tyrosine kinases control cellular functions by means of this phosphorylation mechanism. Tyrosine kinases have a high degree of homology with STKs, including an HJ loop. Consequently, the activity of tyrosine kinases and the cellular functions which they control, can be modulated with peptides which are peptide derivatives of their HJ loops, as discussed above for STKs. Peptides and peptides derivatives of the HJ loop of protein tyrosine kinases and methods of use thereof are disclosed in U.S. Pat. No. 6,723,694, the teachings of which are incorporated into this application.

Peptide sequences in the compounds of the present invention may be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48–267; and Barany and Merrifield, in *The Peptides*, E. Gross and J. Meienhofer, Eds., Academic Press, New York, 1980, pp. 3–285. Methods of solid phase peptide synthesis are described in Merrifield, R. B., *Science,* 232: 341 (1986); Carpino, L. A. and Han, G. Y., *J. Org. Chem.,* 37: 3404 (1972); and Gauspohl, H. et al., *Synthesis,* 5: 315 (1992)). The teachings of these references are incorporated herein by reference.

Methods of cyclizing compounds having peptide sequences are described, for example, in Lobl et al., WO 92/00995, the teachings of which are incorporated herein by reference. Cyclized compounds can be prepared by protecting the side chains of the two amino acids to be used in the ring closure with groups that can be selectively removed while all other side-chain protecting groups remain intact. Selective deprotection is best achieved by using orthogonal side-chain protection such as allyl (OAI) (for the carboxyl group in the side chain of glutamic acid or aspartic acid, for example), allyloxy carbonyl (Aloc) (for the amino nitrogen in the side chain of lysine or ornithine, for example) or acetamidomethyl (Acm) (for the sulfhydryl of cysteine) protecting groups. OAI and Aloc are easily removed by $Pd^\circ$ and Acm is easily removed by iodine treatment.

The invention is illustrated by the following examples which are not intended to be limiting in any way.

EXAMPLE 1

Preparation of HJ Peptides

The novel compounds of this invention can be synthesized utilizing a 430A Peptide Synthesizer from Applied Biosystems using F-Moc technology according to manufacturer's protocols. Other suitable methodologies for preparing peptides are known to person skilled in the art. See e.g., Merrifield, R. B., *Science,* 232: 341 (1986); Carpino, L. A., Han, G. Y., *J. Org. Chem.,* 37: 3404 (1972); Gauspohl, H., et al., *Synthesis,* 5: 315 (1992)), the teachings of which are incorporated herein by reference.

Rink Amide Resin [4(2',4' Dimethoxyphenyl-FMOC amino methyl) phenoxy resin] was used for the synthesis of C-amidated peptides. The alpha-amino group of the amino acid was protected by an FMOC group, which was removed at the beginning of each cycle by a weak base, 20% piperidine in N-methylpyrrolidone (NMP). After deprotection, the resin was washed with NMP to remove the piperidine. In situ activation of the amino acid derivative was performed by the FASTMOC Chemistry using HBTU (2(1-benzotriazolyl-1-yl)-1,1,3,3-tetramethyluronium) dissolved in HOBt (1-hydroxybenzotriazole) and DMF (dimethylformamide). The amino acid was dissolved in this solution with additional NMP. DIEA (diisopropylethylamine) was added to initiate activation. Alternatively, the activation method of DCC (dicyclohexylcarbodiimide) and HOBt was utilized to form an HOBt active ester. Coupling was performed in NMP. Following acetylation of the N-terminus (optional), TFA (trifluoroacetic acid) cleavage procedure of the peptide from the resin and the side chain protecting groups was applied using 0.75 g crystalline phenol; 0.25 ml EDT (1,2-ethandithiol); 0.5 ml thioanisole; 0.5 ml D.I. $H_2O$; 10 ml TFA.

EXAMPLE 2

HJ Peptide Derivatives of Raf and Polo Modulate Proliferation of Endothelial Cells In Vitro Bovine aortic cells (referred to herein as "A19 cells") were obtained by the procedure disclosed in Gospodorowicz et al., *Proc. Natl. Acad. Sci.* 73:4120 (1976)). Mouse MS1 and SVR cells were obtained by the procedures disclosed in Arbiser et al., *Proc. Natl. Acad. Sci.* 94:861 (1997), the teachings of which are incorporated herein by reference.

96 well, flat bottom, tissue culture microtiter plates were precoated with gelatin (Difco) immediately prior to cell plating by adding 0.100 ml/well of freshly filtered 1% gelatin in glass double distilled water (DDW). The wells were incubated for about 1 hour at 37° C., and then the excess solution was removed by aspiration.

Culture medium was prepared from DMEM, pencillin/streptomycin/glutamine (penicillin—100 U/ml; streptomycin—100 µg/mL; and glutamine—2 mM) and 10% endotoxin free bovine calf serum (Hyclone). A suspension of the cell type being tested at $25 \times 10^3$ cells/ml was prepared in the above described culture medium and distributed 0.160 ml/well (about 4000 endothelial cells/well).

A series of HJ peptide stock solutions was prepared by diluting a 10 mM solution of the HJ peptide in 100% DMSO with phosphate buffered saline (PBS)containing 0.1% BSA. The concentration of HJ peptide in each stock solution was adjusted to nine times the desired concentration of the HJ peptide in the assay mixture.

0.020 ml of each HJ peptide stock solution was added to the corresponding wells about 2 hours after cell plating, with six replicates for each concentration. In addition, BSA solution with no added HJ peptide was used as a control. The wells were incubated for 72–80 hours at 37° C. in a 10% $CO_2$ humidified incubator.

The plates were labeled and the medium discarded. Each plate was then washed one time with PBS (0.200 ml/well). The wells were then fixed by washing with 100% ethanol (0.200 ml/well for 5 minutes). The ethanol was removed and the wells dried completely. Alternatively, the wells were fixed with 4% formaldehyde PBS (PBS buffered 10% formalin from Fisher Scientific; Catalog No. HC200-1) (0.12 ml/well) for at least 30 minutes. Fixing with formaldehyde enhances the O.D. compared with ethanol.

The wells were washed one time with borate buffer (0.1 M, pH 8.5). Freshly filtered 1% methylene blue solution (0.600 ml/well) was then added to the wells and incubated for 10 minutes at room temperature. The wells were then washed five times with tap water, after which the wells were dried completely. 0.200 ml/well of 0.1 N HCl (0.1 N) was added to extract the color. After extracting overnight, the O.D. was read at 630 nm to determine the number of cells per well. The procedure for counting cells is described in greater detail in Oliver et al., *J. of Cell Sci.*, 92:513 (1989), the teachings of which are incorporated herein by reference.

The results for a number of different HJ peptides are shown in the Table.

TABLE

| Peptide | S.I.* (µM) for SVR Cells | S.I.* (µM) for MSI Cells | S.I.* (µM) for A19 Cells |
|---------|--------------------------|--------------------------|--------------------------|
| HJ38    | 10                       | 10                       | Not Tested               |
| J41     | Not Tested               | 10                       | Not Tested               |
| J42     | 10                       | Not Tested               | 10                       |
| J43     | Not Tested               | Not Tested               | 40                       |

*Concentration at which significant inhibition of cell proliferation was observed.

As can be seen from the results in the Table, HJ peptide derivatives of Raf and Polo inhibited cell proliferation of bovine aortic cells and the transformed mouse cell lines MS1 and SVR.

EXAMPLE 3

The HJ Peptide Derivative of Activin/TGFbR K048H101 (SEQ ID NO.: 24) Inhibits the Production of Collagen by Fetal Lung Fibroblasts Cells Fetal lungs fibroblasts are suspended in DMEM medium containing 0.5% FCS and seeded in a 96-well flat bottom tissue culture plate at a density of 50,000 cells per well (45 µl per well). The cells are incubated for 48 hours in the presence of 45 µl of heat activated TGFβ-containing condition medium (collected from MCF-7 cells), and in the absence or presence of increasing concentrations of the tested peptide (0–10 µM in 10 µl PBS+0.1% BSA+1% DMSP). The total volume is 100 µl per well.

Soluble Collagen

At the end of the incubation period, supernatants are removed and plated in 50 µl per well aliquots into a new tissue culture plate. The plate is incubated at 37° C. for 24 hours in a humid atmosphere to allow collagen adhesion then dried at 37° C. for 24 hours. The dry plate is washed 3 times with distilled water, 200 µl per well and 1 minute per wash and stained with 100 µl of 0.1% direct red 80 in saturated picric acid (w/v) per well, for 1 hour at room temperature. Excess dye is removed by washing the wells 5 times with 10 mM HCl, 200 µl per well and 10 sec per wash. Collagen-bound stain is eluted with 200 µl of 0.1M NaOH per well, and read at 540 nM.

Cell Count

Subsequent to the supernatant removal, the cells are fixed with 200 µl buffered formaline per well, for 1 hour at room temperature and then washed with 200 µl of 0.1M borate buffer per well. The fixed cells are stained with 50 µl 1% methylene blue per well, for 15 minutes at room temperature. Excess dye is washed with tap water. Cell-bound dye is eluted with 200 µl of 0.1M HCl per well, and read at 595 nm. Collagen is expressed per cell.

The results for K048H101 (SEQ ID NO.: 24) are shown in FIG. 5. As can be seen from FIG. 5, nearly complete inhibition of collagen production occurs at concentrations as low as 1 µM of K048H101. About 80% inhibition occurs in the presence of about 0.6 µM K048H101.

The inhibition of collagen-formation might be useful for the inhibition of scar-formation, e.g. in plastic surgery and for the inhibition of adhesion-formation, a major complication of abdominal surgery.

EXAMPLE 4

The HJ Peptide Derivative of Integrin-Linked Kinase (ILK) K107H101 (SEQ ID NO.: 47) Causes Morphological Changes in B16 Melanoma Cells A change of morphology of B16 melanoma cells was observed when incubated in the presence of K107H101, a peptide derived from the HJ-loop of the serine-threonine kinase named integrin-linked kinase (ILK). As described in Wu C. et al., *J. Bio. Chem.* 273:528–536 (1998), ILK is implicated in tumor formation. Therefore, ILK-derived peptides might be useful as anti-tumor agents. The entire teachings of Wu et al. are incorporated herein by reference.

Equivalents

Those skilled in the art will be able to recognize, or be able to ascertain, using no more than routine experimentation, many equivalents to the specific embodiments of the invention described herein. Such equivalents are intended to be encompassed by the following claims.

What is claimed is:

1. A method of modulating the activity of a member of the polo serine/threonine kinase family in a subject, comprising administering to said subject an amount effective to modulate the activity of the serine/threonine kinase in the subject of a peptide having the sequence of J-42 (SEQ ID NO.: 15), J-43 (SEQ ID NO.: 16), J-43.1 (SEQ ID NO.: 17), J-45 (SEQ ID NO.: 18) or J-46 (SEQ ID NO.: 19).

* * * * *